US00RE37970E

(19) United States
(12) Reissued Patent
Costello, Jr.

(10) Patent Number: US RE37,970 E
(45) Date of Reissued Patent: Jan. 28, 2003

(54) PULSE OXIMETRY TESTING

(75) Inventor: Leo F. Costello, Jr., Madison, CT (US)

(73) Assignee: Clinical Dynamics Corporation, Wallingford, CT (US)

(21) Appl. No.: 09/620,641

(22) Filed: Jul. 21, 2000

Related U.S. Patent Documents

Reissue of:
(64) Patent No.: Re. 36,620
Issued: Mar. 21, 2000
Appl. No.: 09/172,586
Filed: Oct. 14, 1998

Which Is a Reissue of:
(64) Patent No.: 5,783,821
Issued: Jul. 21, 1998
Appl. No.: 08/962,149
Filed: Oct. 31, 1997

U.S. Applications:
(63) Continuation of application No. 08/556,749, filed on Nov. 2, 1995, now abandoned.

(51) Int. Cl.[7] ..... G01L 25/00
(52) U.S. Cl. ..... 250/252.1
(58) Field of Search ..... 250/252.1, 343; 356/40, 41, 42; 128/633

(56) References Cited

U.S. PATENT DOCUMENTS

| | | | |
|---|---|---|---|
| 4,700,708 | A | 10/1987 | New, Jr. et al. |
| 4,831,626 | A | 5/1989 | Watanabe et al. |
| 4,834,532 | A | 5/1989 | Yount |
| 4,968,137 | A | 11/1990 | Yount |
| 5,134,284 | A | 7/1992 | Volgyesi |
| 5,136,280 | A | 8/1992 | Haggli |
| 5,166,517 | A | 11/1992 | Volgyesi |
| 5,278,627 | A | 1/1994 | Aoyagi et al. |
| 5,348,005 | A | 9/1994 | Merrick et al. |

OTHER PUBLICATIONS

"Technical Manual Nellcor Puritan Bennett TM Pulse Oximeter Tester Model SRC–2", 1996.

Criticare—Oxygen Saturation Simulator, Special Offer Sheet plus pp. 2–1, 2–2, 2–3, and 2–4 plus Circuit Diagram Sheet 1/1 titled Sp02/ECG Simulator (EProm Version) Oct. 6, 1991.

Novametrix TB500B Front Panel, Service Manual, p. 3, Nov. 11, 1992.

*Primary Examiner*—David P. Porta
(74) *Attorney, Agent, or Firm*—Leo F. Costello

(57) ABSTRACT

A method and apparatus for testing a pulse oximeter which is based on the concept of an electrical interface between the testing instrument and the oximeter rather than an optical interface. The pulse oximeter signal processor is tested separately from the probe, and still further, the optical elements, that is, the LEDs and the photodiode, of the probe are tested separately from the probe cable. With the probe disconnected from the oximeter, a modulated electrical test signal representative of $SpO_2$ values and other parameters is generated in response to an electrical signal from the oximeter, and the test signal is applied to the oximeter signal processor, whereby the display of the oximeter shows a value of $SpO_2$ which is compared with the $SpO_2$ value represented by the test signal. Independently, the probe including the probe cable, the LEDs and the photodiode are respectively and separately subjected to continuity and optical sensitivity tests. Each of the main components of the oximeter is thereby separately analyzed, and the source of a defect is isolated.

92 Claims, 12 Drawing Sheets

PULSE OXIMETRY TESTING

Matter enclosed in heavy brackets [ ] appears in the original patent but forms no part of the first and this reissue specification; matter printed in italics indicates the additions made by the first reissue. Matter enclosed in double heavy brackets [[ ]] appears in the first reissue patent but forms no part of this reissue specification; matter printed in bold face indicates the additions made by this reissue.

This application is a *REISSUE of Ser. No. 08/962,149 filed Oct. 31, 1997 U.S. Pat. No. 5,783,821, which is a* continuation of application Ser. No. 08/556,749, filed Nov. 2, 1995, now abandoned.

FIELD OF THE INVENTION

This invention pertains to pulse oximeter testing and more particularly to a method and apparatus for testing pulse oximeters.

BACKGROUND

Pulse oximeters are commonly used in hospitals and other patient-care facilities for monitoring the blood oxygen level of a patient in a non-invasive, continuous manner. The basis of operation of these instruments is the fact that blood absorbs red (R) and infrared (IR) light in different amounts depending on the level of oxygen in the blood ($SpO_2$) and that a known relationship exists between the ratio of red to infrared light (R/IR) and blood oxygen level ($SpO_2$).

Thus, a pulse oximeter functions by detecting the amount of red and infrared light transmitted through a part of the body, usually a finger, to establish the R/IR ratio. It then compares this ratio with an internally stored database giving the relationship between R/IR ratios and $SpO_2$ levels, determines the $SpO_2$ level for the detected ratio, and displays the $SpO_2$ value. Pulse rate and other parameters may also be detected and displayed.

The popular pulse oximeters provide an optical sensor, typically called a probe, which is an alligator- or clamshell-clip that clamps on the index finger of a patient. One jaw of the probe clip contains red and infrared light-emitting diodes (LEDs), and the other jaw contains a light-detector such as a photodiode. The probe cable is connected to the main unit or instrument of the oximeter. Certain of the conductors in the cable connect the LEDs to a driver circuit in the instrument which produces a signal to activate the LEDs, and other conductors connect the photodiode to an amplifier for amplifying the small signal generated by the photodiode when light is transmitted through a finger and for transmitting it to the signal processor of the oximeter.

Like any instrument for monitoring physiological functions, a pulse oximeter needs to be tested on a regular basis to determine if it is providing accurate readings. Although test equipment has been developed for testing the accuracy of pulse oximeters, such equipment has been based on a particular testing philosophy which imposes certain undesirable limitations on the test results. This philosophy is to provide a simulated finger, clamp this "finger" in the oximeter probe, operate the oximeter to test the simulated finger just as if it were a real finger, and determine if the display provides a reading consistent with the simulation. An example of this testing approach is disclosed in the Merrick et al. U.S. Pat. No. 5,348,005. In this patented device, the artificial finger is a long, narrow, finger-shaped object made of steel and having slots on opposite sides respectively receiving an LED bar and a pair of photodiode detectors. To test an oximeter, the Merrick et al. artificial finger is placed in the oximeter probe, and the oximeter is operated just as if it were monitoring a human subject. That is, the red and IR LEDs of the oximeter emit flashes of light that are detected in the "finger" by the photodiodes which convert the light pulses into electrical pulses. These pulses are modulated in the tester to provide signals which simulate the signals that would be developed from a human finger. The modulated electrical signals are then transmitted to the LEDs in the artificial finger which converts them to light flashes that activate the photodiode in the oximeter probe. Thus, the artificial finger is an optical interface between the oximeter under test and the test equipment.

The described testing approach is certainly the straightforward approach in that it simply replaces a real finger with an artificial finger and allows the oximeter to be used for the test in a manner similar to its use in monitoring a patient. The only difference appears to be the use of an electro-optical finger instead of a real finger. Such an approach, however, has not proved to be fully effective since the reliability of the testing can be compromised or indeterminate and desired testing flexibility is lacking, as hereinafter explained.

First, the testing accuracy of an oximeter tester using an optical interface, as described above, depends on proper placement of the simulated finger in the probe to allow the optical elements to interact properly. With a human finger, exact placement of the finger in the probe is not critical since the entire circumference of a finger presents human tissue to the LEDs. With an artificial finger, however, the photodiodes and the LEDs in the artificial finger must be placed exactly opposite the LEDs and photodiode, respectively, of the probe or else the light flashes will not be detected by the photodiodes. Thus, if this placement is not exact, inaccurate readings will occur.

Before discussing other deficiencies of oximeter test equipment employing an optical interface, it is important initially to understand the construction of commonly used oximeter cables and their normal use in a hospital. The cable referred to in one popular brand of oximeter is actually two cables, namely, a preamp cable and a probe cable. Although interconnected, these two cables are of different construction; the preamp cable is relatively strong and durable, whereas the probe cable is not as strong or durable. The preamp cable is a thicker, somewhat flexible, heavy duty cable, usually about 12 feet long, whereas the probe cable is a thinner, very flexible, lightweight cable, usually about 3 feet long. Whether or not the oximeter has a preamp cable, extension cables (also referred to as patient cables) are often provided and for the purpose of the present invention are equivalent to a preamp cable. In referring to the preamp cable hereinafter, it will be understood that such an extension cable is included.

The preamp cable is normally attached to and kept with its oximeter instrument as the latter is moved about the hospital, whereas the probe cable is normally kept separate from the oximeter instrument and is not associated with any particular instrument since it can be attached to any instrument of the same manufacture. The probe cable may even be a disposable item.

In a hospital room, the preamp cable is long enough to serve as an extension cord so that the oximeter instrument can be placed in a convenient position and the preamp cable stretched to the bedside of the patient. In contrast, the probe cable is clamped to the bed or bedclothes of the patient's bed and coupled to the preamp cable. The probe cable is made light and flexible so that it moves easily and folds as the patient moves about and is less of an annoyance to the patient. Thus, probe cables can easily fall on the floor by the bedside and be subjected to abuse. Moreover, they are normally folded, wound, or otherwise compressed and stored in a drawer, sometimes rather haphazardly.

Because of the described construction, use and treatment of probe cables and their probes, they are very vulnerable to damage and defects. Field studies with hospital biomedical technicians have shown that the majority of oximeter defects have been probe defects and that these defects are caused by frayed probe cable wires, that is, breaks or shorts, many of which occur intermittently. Compounding this problem is the fact that as indicated above, specific oximeter probes are not paired with specific oximeter instruments, that is, the probes are interchangeable among different oximeters and as stated above, the entire probe including the cable and the clip may be disposable.

Using the above described testing approach with an optical interface, i.e., inserting an artificial finger in the clamshell probe of the pulse oximeter, the testing device performs the test through the probe cable, that is, with the probe cable connected to the preamp cable, just as if the oximeter were being used on a human patient. If there is a defect in the probe cable, this testing approach may miss it or fail to isolate it.

For example, if the probe cable has frayed wires, front end circuitry in the oximeter may filter out the noise spikes caused by the fraying, and the display will indicate normal functioning, whereas in fact the probe cable is damaged and may later fail completely at a critical time. Moreover, if the display on the tester indicates an erroneous reading, it may not be possible to determine if the problem is in the probe including the probe cable, or in the signal processing circuitry. Furthermore, if the source of the problem is suspected to be in the probe, the tester provides no way of separately testing the probe cable and optics on the one hand, and the signal processing circuitry on the other hand, to isolate the problem area.

Thus, testing the oximeter as an integral entity, i.e., the probe and signal processing circuitry together, as the optical-interface approach requires, does not afford an unqualified independent assessment of these main parts, and especially of the parts most likely to fail. In fact, this testing methodology may introduce other problems as explained above. In contrast, the oximeter testing approach of the present invention differs from optical interface concept described above and, as a result, avoids the resultant problems.

SUMMARY

Pulse oximeter testing according to the present invention is based on the concept of an electrical interface between the testing instrument and the pulse oximeter rather than an optical interface. Thus, the subject method and apparatus involve testing a pulse oximeter signal processor separately from the probe, and still further, testing the continuity of the probe, particularly the probe cable, separately from the sensitivity of optical elements of the probe.

For testing according to the present invention, the probe is disconnected from the pulse oximeter. Then, a modulated electrical test signal representative of blood oxygen saturation values is generated in response to the electrical LED drive signal from the oximeter and is electrically applied to the oximeter signal processor. This signal causes the display of the oximeter to show a value of blood oxygen saturation which is compared with the saturation values represented by the test signal. Other parameters, such as pulse rate and pulse amplitude, may also be tested. Independently of the signal processor test, but simultaneously therewith if necessary, the probe is subjected to continuity and sensitivity tests and the results displayed. In this manner, each of the main components of the pulse oximeter is separately analyzed, and the source of a defect, if any, is isolated.

An object of the present invention is to test and verify the basic operation of pulse oximeters used in hospitals and other patient care facilities.

It is another object to test pulse oximeters in a more efficient, effective, safe, and reliable manner than heretofore known.

Another object of the subject invention is to avoid the errors which may be introduced into the testing of a pulse oximeter when the oximeter is tested by clamping its probe onto a simulated finger containing optical elements, thus requiring precise positioning of the simulated finger in the probe.

Another object is to use an electrical, instead of an optical, interface between the pulse oximeter and an instrument for testing the oximeter.

A still further object is to be able to test the main components of a pulse oximeter, namely, the oximeter electronic unit and the optical sensor, separately from each other.

Yet another object is to test a pulse oximeter so as to isolate the source of defects among the main parts of the oximeter.

Still another object is to facilitate testing both the continuity of the probe and the optical functions of the probe independently of each other and of the signal processing circuitry of a pulse oximeter.

Another object is to eliminate doubts about the integrity of testing a pulse oximeter which tests good although its probe cable may have a emerging discontinuity causing intermittent noise spikes which are filtered out by the oximetry circuitry but which could eventually degrade and cause inaccurate or no readings during critical use of the oximeter.

A further object is to be able to test oximeter probes, which are interchangeable among different oximeters, independently of the main oximeter test instrument.

A still further object is to be able to test an oximeter probe, which are the source of most of the defects in an pulse oximeter.

An additional object is to display waveforms representative of the tests performed on the continuity of the probe of a pulse oximeter and on sensitivity of the optical elements of the probe alone while at the same time displaying digital readouts of blood oxygen level, pulse rate and other parameters being tested.

Yet another object is to provide an apparatus for testing a pulse oximeter which is able to test the most commonly used pulse oximeters.

A still further object is to simplify the task of biomedical equipment technicians and other trained healthcare personnel in testing the basic operation of pulse oximeters used in hospitals and other patient-care facilities.

Another object is to be able to subject a pulse oximeter to a manually or automatically controlled sequence of test signals including predetermined combinations of blood oxygen saturation and other parameters, such as pulse rate and pulse amplitude, representing either arbitrary test values or patient profiles, and to determine the response to the oximeter.

A feature of this invention is to allow defects in the probe cable of a pulse oximeter to be analyzed to determine if the cable can be used, should be disposed of, or should be set aside for repair.

An additional feature of this invention is to allow the optical elements of the probe cable of a pulse oximeter to be analyzed to determine if the probe can be used, should be disposed of, or should be set aside for repair.

DETAILED DESCRIPTION OF THE APPARATUS

Figure 1:
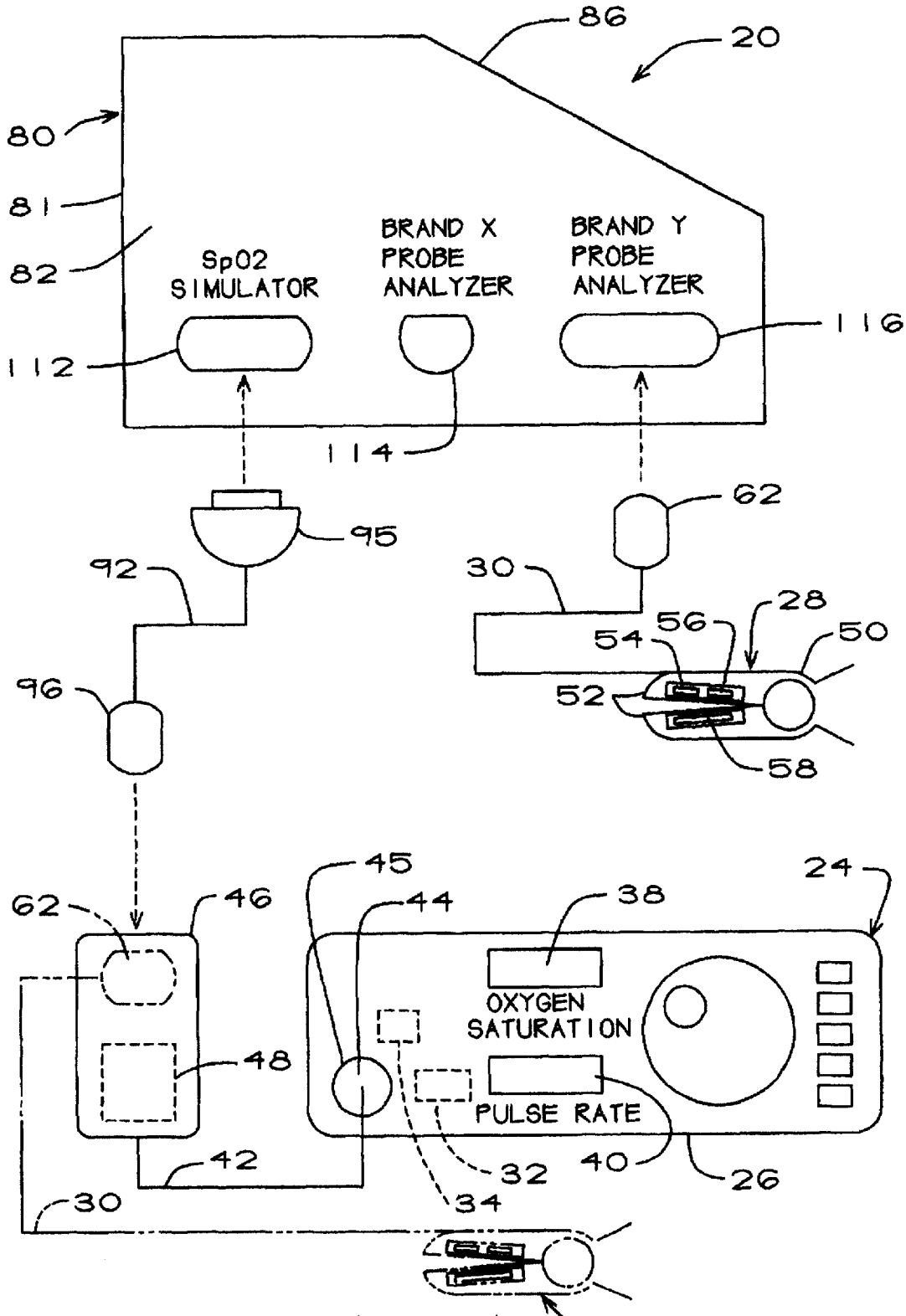
FIG. 1 is a schematic drawing showing a left side elevation of a main unit or instrument of the pulse oximeter testing apparatus of the present invention and showing the apparatus in readiness to be connected to a commonly used pulse oximeter, with the probe disconnected from the oximeter and in position to be connected to the subject testing apparatus but also showing in phantom lines the probe as it is normally connected to the pulse oximeter through the preamp cable.
Figure 2:
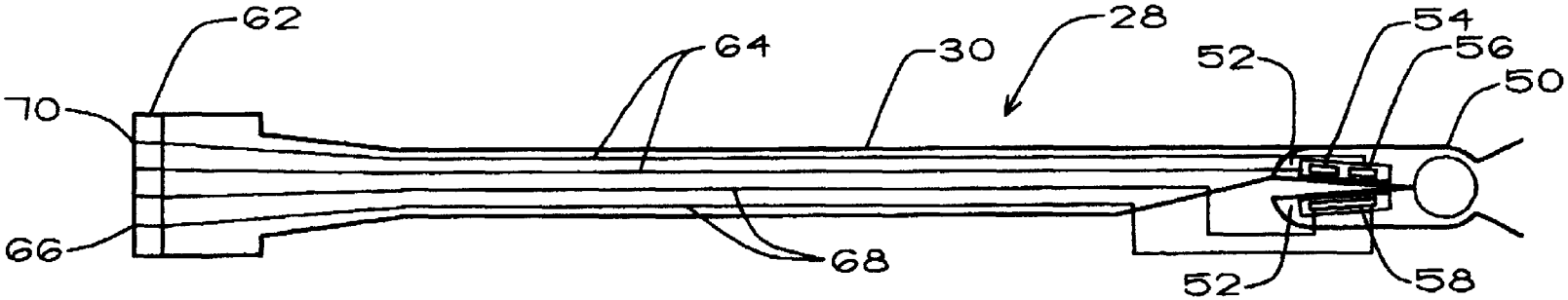
FIG. 2 is a diagrammatic view of the probe of FIG. 1 which includes a probe connector, a probe cable and a finger clamp.

The pulse oximeter testing apparatus or analyzer of the present invention is generally represented by the numeral 20 in FIG. 1, which is a schematic drawing showing how the testing apparatus is connected to a pulse oximeter 24. Since reference will made herein to certain aspects of the pulse oximeter itself, it will be helpful at the outset to provide a brief general description of a typical pulse oximeter.

Thus, the pulse oximeter 24 (FIG. 1) includes a main unit 26 and a probe 28 which includes a probe cable 30. The main unit includes a signal processor 32, an LED driver 34, and upper and lower displays 38 and 40 for displaying the blood oxygen saturation $SpO_2$ as a percentage and pulse rate in beats per minute. The main unit of the brand of oximeter shown and described herein also includes a preamp cable 42. The preamp cable terminates at one end in a proximal preamp connector 44 coupled to an interface connector 45 in the main unit 26 and at the opposite end in a distal. preamp connector 46. A photodiode amplifier 48 is located in the distal preamp connector. Some brands of oximeter do not employ an external photodiode amplifier but incorporate all the necessary functions in the main unit. The principles of the present invention are equally applicable whether or not the oximeter uses an external preamplifier and cable.

Figure 4:
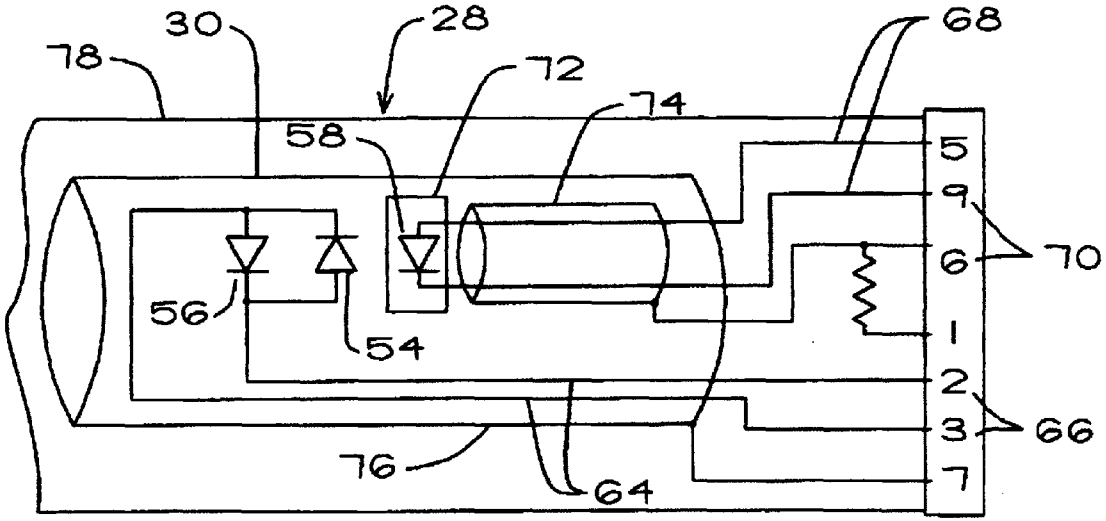
FIG. 4 is another diagrammatic view of the probe and its components.
Figure 3:
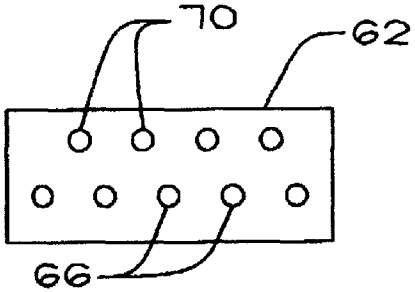
FIG. 3 is a detailed face view of the probe connector.
Figure 5:
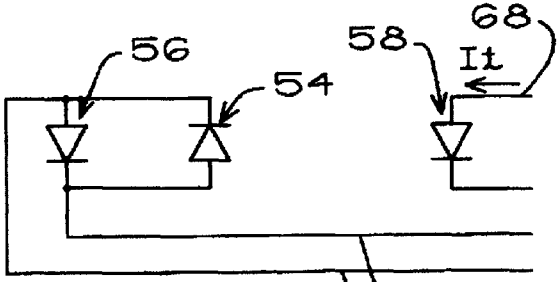
FIG. 5 is a schematic diagram of the red and IR LED circuit and the photodiode circuit in the probe of FIGS. 2–4.
Figure 6:
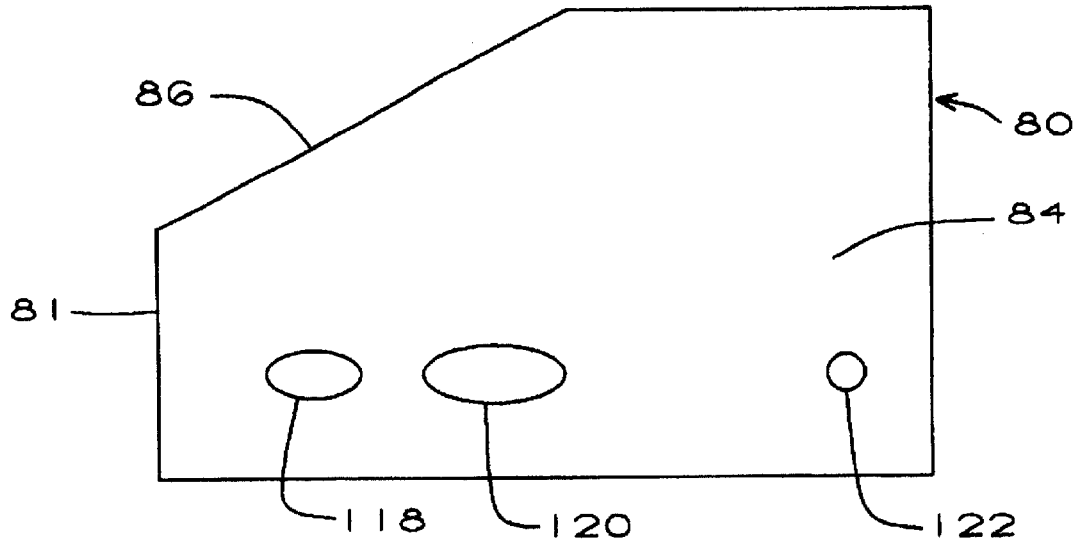
FIG. 6 is a right side elevation of the main unit of the pulse oximeter testing apparatus of FIG. 1.

The probe 28 including the probe cable 30 is shown in greater detail in FIGS. 2–5 to which reference is now made. The probe includes a clamshell- or alligator-clamp or clip 50 which has hinged upper and lower jaws 52. Red and infrared light-emitting diodes (LEDs) 54 and 56, respectively, are mounted in the upper jaw, and a photodiode 58 is mounted in the lower jaw. The LEDs are electrically connected in inverse parallel relationship as shown in FIGS. 4 and 5 and are positioned in the clamp so as to direct light toward the photodiode. As is well-known, when the oximeter 24 is used to monitor the blood oxygen level ($SpO_2$) of a patient, the probe clamp is clipped onto the index finger of the patient so that light from the LEDs can be transmitted through the finger and be detected by the photodiode.

A probe connector 62 (FIGS. 2 and 3) is attached to the probe cable 30 at the opposite end from the probe clamp 50. In the normal operation of the oximeter, the probe connector 62 is connected to the distal preamp connector 46, as shown in phantom in FIG. 1, thereby to connect the probe 28 to the main unit 26. In accordance with the principles of the present invention, however, the probe connector 62 connects the probe to the subject testing apparatus 20, as will be subsequently described in detail.

The probe cable 30 (FIGS. 2–5) includes LED conductors 64 interconnecting the LEDs 54, 56 and terminals 66 in the probe connector 62, thereby constituting an LED circuit, and photodiode conductors 68 interconnecting the photodiode 58 and other terminals 70 in the connector, thereby constituting a photodiode circuit. The probe cable also includes electromagnetic shields 72, 74, and 76 (FIG. 4) and outer insulation 78, all of which are well-known and thus not described in greater detail.

With the foregoing brief description of a typical oximeter 24 is background, reference is now made to the testing apparatus 20 (FIGS. 1 and 6–8) of the present invention. The testing apparatus provides a main instrument 80 which includes a housing 81 that has a left panel 82, a right panel 84, and a front panel 86, and which encloses an electronic testing system generally identified by the numeral 90 in FIG. 8. The testing apparatus also includes a simulator adapter cable 92 (FIGS. 1 and 8) and an external DC power supply 94. The simulator adapter cable has connector plugs 95 and 96 at opposite ends thereof.

Figure 12:
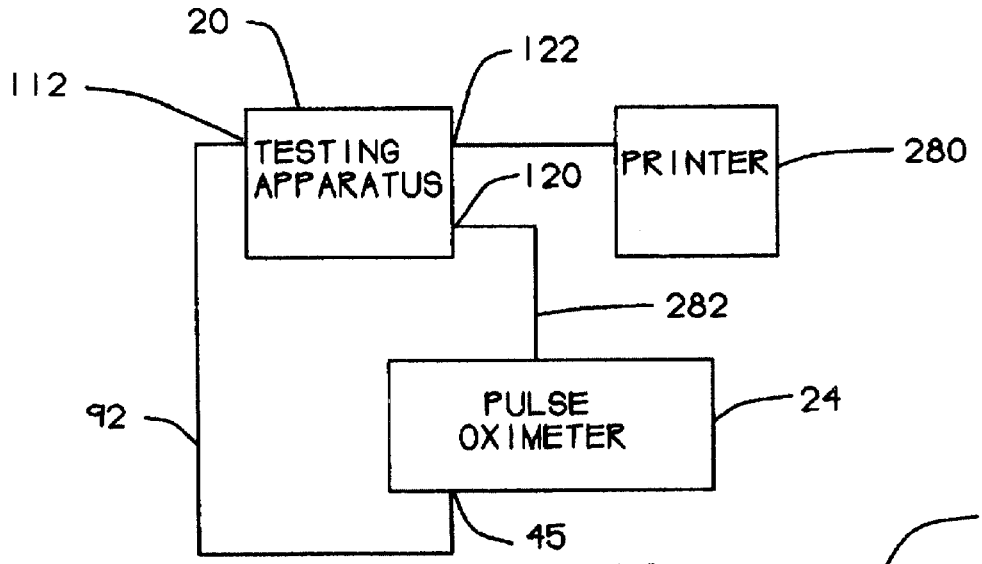
FIG. 12 is a functional block diagram showing how the testing apparatus is connected to an oximeter and a printer for automatically logging the results of a test.

The electronic testing system 90 (FIG. 8) provides an $SpO_2$ simulator or signal processor 100; a probe analyzer 102; a microprocessor 104; a user interface 106; an internal power supply with battery 108; and interface connectors 112, 114 and 116 (FIG. 1) in the left panel 82. Interface connector 112 is connected to the $SpO_2$ simulator, and interface connectors 114 and 116 are connected to the probe analyzer respectively for brand X and brand Y pulse oximeter probes 28. The interface connector 112 is designed to receive the plug 95 of the simulator adapter cable 92, and interface connectors 114 and 116 are designed to receive the connectors 62 of the probe cables 30 of the manufacturers of brand X and brand Y oximeters, as 24. Interface connectors 118, 120, and 122 (FIG. 6) are mounted in the right panel 84 respectively for the external DC power supply 94, for serial communication, and for a printer (FIG. 12).

Figure 7:
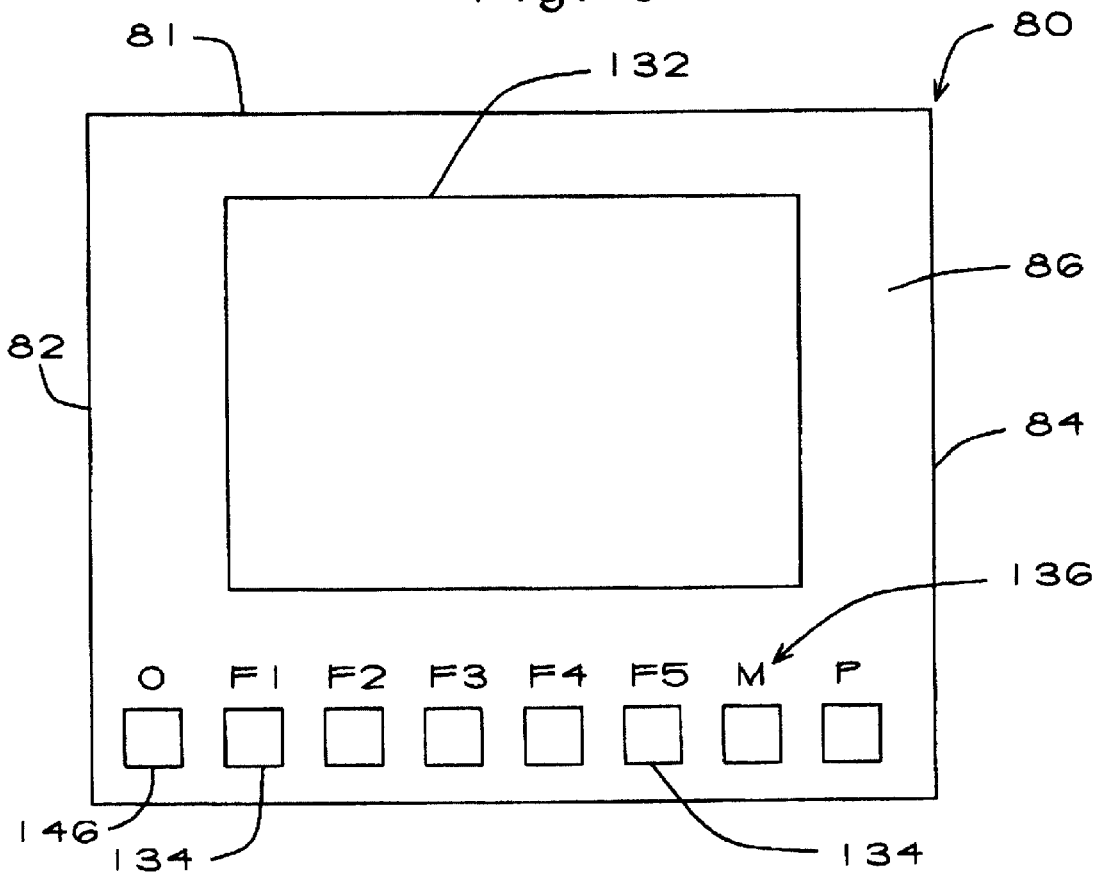
FIG. 7 is a front elevation of the main unit shown in FIGS. 1 and 6.

To best understand the testing functions of the subject apparatus 20, it will be helpful first to explain the user interface 106 (FIGS. 7, 8 and 13–15). The user interface includes an LCD graphic display subsystem 130 (FIG. 8) which provides an LCD display screen or panel 132 (FIG. 7 and 12–15) in the front panel 86 of the housing 81 and a plurality of keys 134 in a keypad 136 below the screen. The display screen is divided into an upper $SpO_2$ simulator window 140, a middle graphing window 142, and a lower soft-key menu window 144. In the disclosed embodiment, there are five soft keys F1–F5, two hard keys M and P, and an on/off key O (FIG. 7).

Figure 13:
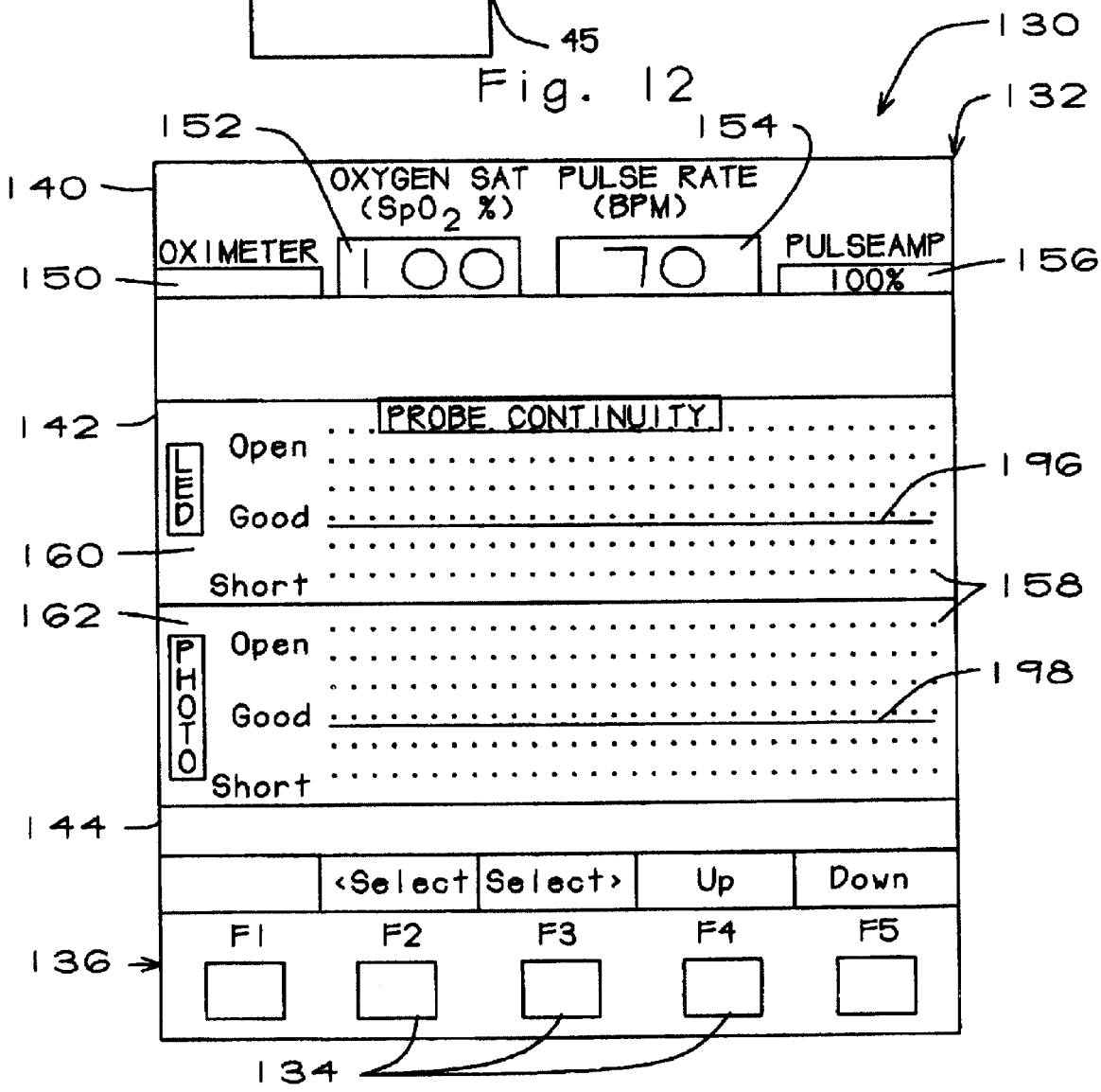
FIGS. 13, 14, and 15 are diagrammatic views of the display screen and part of the keypad of the subject testing apparatus showing different displays and different menus which are available on the display screen with the method and apparatus of the present invention.
Figure 14:
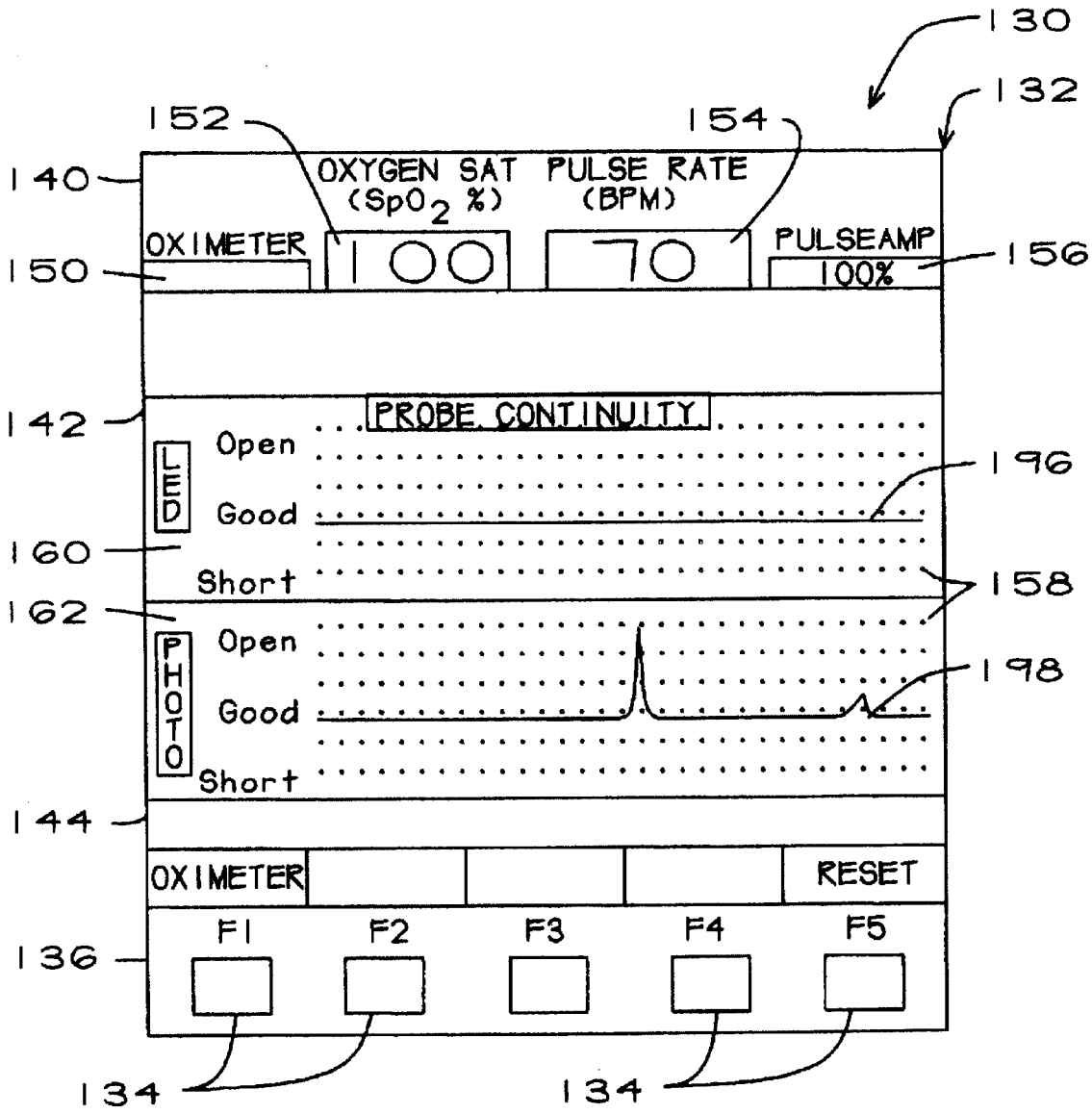
Figure 15:
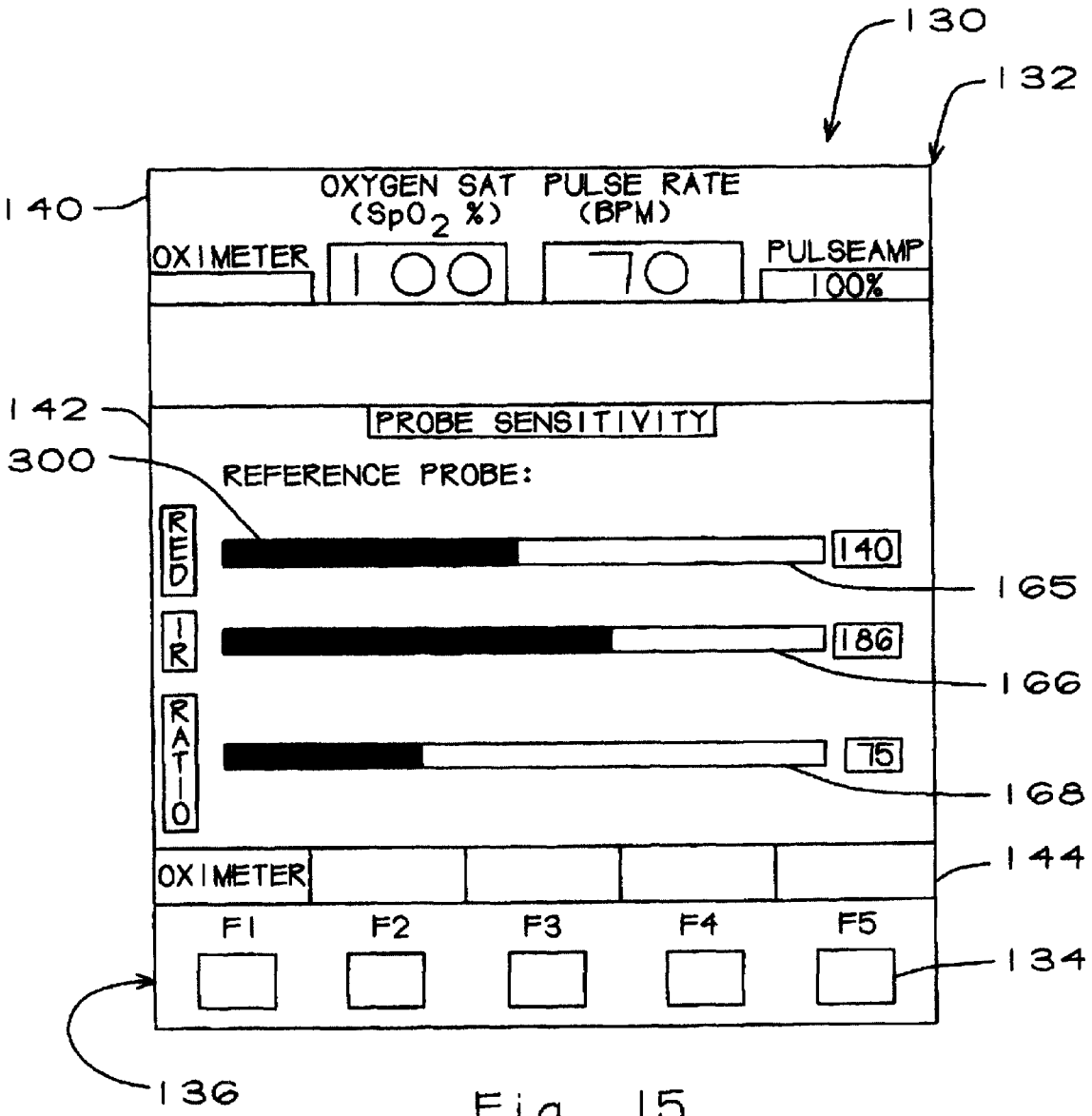

The LCD graphic display subsystem 130 (FIGS. 8 and 13–15) provides several menus to be displayed in the lower menu window 144, and these menus are selected by pressing the hard keys M and P. In the disclosed embodiment, there is one root menu and four sub-menus, namely, an $SpO_2$ simulator sub-menu (FIG. 13), a sequencing sub-menu, a probe continuity sub-menu (FIG. 14), and a probe sensitivity sub-menu (FIG. 15). For each menu displayed, each soft key F1–F5 has a different function which is displayed in the lower menu window above the key, as shown in FIGS. 13, 14 and 15. The root menu is not shown, but it is the default menu in which the names of the four sub-menus are displayed in the lower menu window above the keys F1 through F4. The sub-menus correspond to the different modes of operation of the subject testing apparatus 20, namely, $SpO_2$ simulator mode, sequencing mode, probe continuity mode and probe sensitivity mode and relate to the displays in the upper and middle windows 140 and 142. The $SpO_2$ simulator menu relates to the upper or $SpO_2$ simulator window 140, whereas the sequencing, probe continuity, and probe sensitivity submenus all relate to the middle or graphing window 142.

Figure 8:
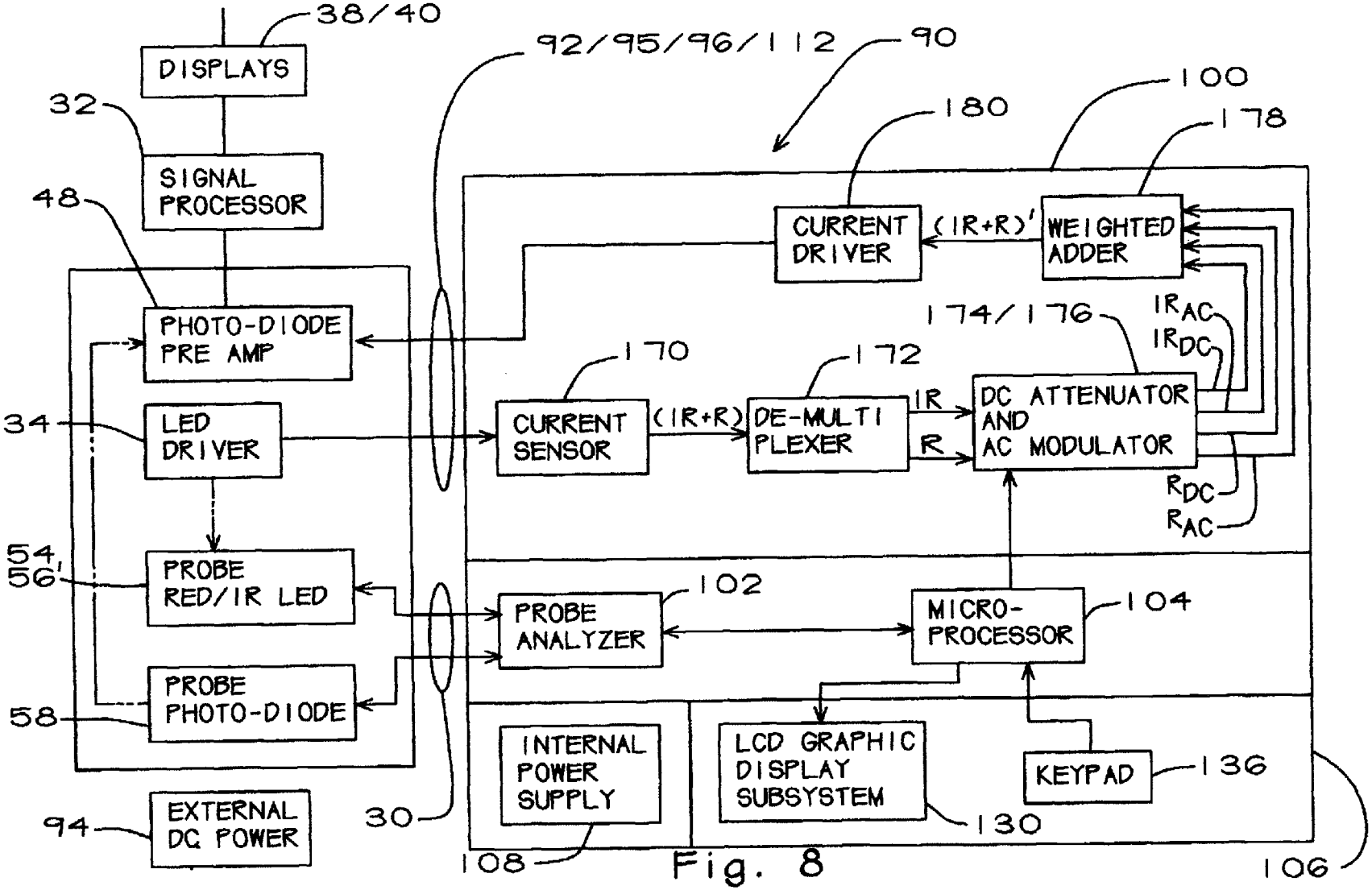
FIG. 8 is a functional block diagram showing the major components of the subject testing apparatus and their connections to a pulse oximeter under test.

Considering first the $SpO_2$ simulator mode using the $SpO_2$ simulator sub-menu and its related upper, $SpO_2$ simulator window 140 (FIG. 13), the latter displays the parameter settings selected and then generated by the $SpO_2$ simulator 100 (FIG. 8). The $SpO_2$ window includes an oximeter brand or status box 150, which displays the brand of oximeter under test; an oxygen saturation display box 152, which displays $SpO_2$ as a percentage; a pulse rate display box 154, which displays pulse rate in beats per minute; and a pulse amplitude display box 156, which displays pulse amplitude as a percentage. Examples of typical values are shown in boxes 152, 154, and 156.

Using the $SpO_2$ simulator sub-menu (FIG. 13), the display boxes 152–156 are sequentially highlighted and thus selected by pressing soft keys F2 or F3. When the $SpO_2$ box 152 is selected, the desired $SpO_2$ percentage can be chosen by pressing the keys F4 or F5 which causes the percentage displayed s to increase or decrease in increments of one percent. The $SpO_2$ percentage displayed corresponds to a particular R curve (relationship between R/IR and $SpO_2$) stored in the microprocessor and selected when keys F4 or F5 are pressed. Similarly, the pulse rate and pulse amplitude are selected and displayed in the boxes 154 and 156.

As previously indicated, the sequencing, probe continuity and probe sensitivity modes all share the middle or graphing window 142. Each of these modes, along with its sub-menu, is selected by pressing the hard keys M or P. For the probe continuity mode, the key M or P is pressed until the probe continuity sub-menu appears in the lower window 144 (FIGS. 13 and 14) and the probe continuity display 158 appears in the middle window 142 (also FIGS. 13 and 14). The probe continuity display provides an upper LED channel 160 and a lower photodiode channel 162, both extending across the window. The graphic display subsystem 130 provides a static graphic background for the probe continuity display including: a matrix of dots or graticules (FIG. 13) spaced horizontally in time preferably by five milliseconds; the indicia "LED" and "PHOTO" along the ordinate margins of the upper and lower channels, respectively; the indicia "OPEN", "GOOD", and "SHORT" along the ordinate margin of each channel; and the label "PROBE CONTINUITY" along the top of the window. For the probe sensitivity mode, one of the keys M or P is pressed until the probe sensitivity display 164 shown in FIG. 15 appears in the middle or graphing window 142 and the probe sensitivity sub-menu appears in the lower window 144. For the probe sensitivity mode, the graphic display subsystem 130 provides a static graphic background in the middle window including: upper, middle and lower bargraph channels 165, 166, and 168 which, although not shown, are empty when no test is being conducted; the indicia "RED," "IR," and "RATIO" along the left margin; the label "PROBE SENSITIVITY" along the top of the window; the name of the probe 28 being tested just below the label; and areas at the right ends of the bargraph channels to display numbers respectively representative of the amplitudes of the values displayed in the bargraph channels.

As for the sequencing mode and sub-menu, more detailed reference is made under the subsequent heading "Test the Main Unit-Sequencing Mode." With the foregoing understanding of the user interface 106, the $SpO_2$ simulator 100 (FIG. 8) of the subject testing apparatus 20 includes a current sensor 170 as its input stage. When the testing apparatus is being used to test the pulse oximeter 24, the connector 62 of the probe cable 30 (FIG. 1) is disconnected from the preamp connector 46, and instead, the simulator adapter cable 92 is connected to the preamp connector and also to the interface connector 112, thereby establishing an electrical connection between the input of the current sensor and the output of the LED driver 34 of the pulse oximeter under test.

Figure 8A:
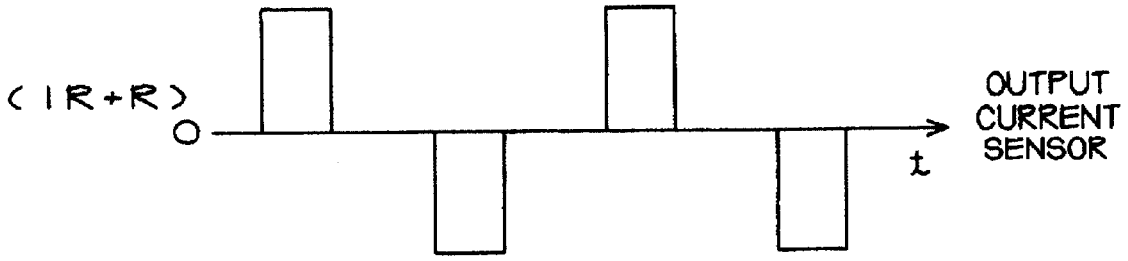
FIGS. 8A–8D are pulse timing diagrams showing IR and red voltage pulses occurring in the circuits of FIG. 8, and FIGS. 8E and 8F are Pleth diagrams which are illustrated to assist in explaining the circuits of FIG. 8, it being noted that, for illustrative purposes, the scale of the pulses in FIG. 8D differs from FIGS. 8A–8C.

When the testing apparatus 20 is thus connected to the pulse oximeter 24 under test (FIG. 1) and the oximeter 24 is powered up, the LED driver 34 (FIG. 8) will then feed red and IR current pulses to the current sensor 170 instead of to the probe LEDs 54 and 56. The current sensor receives these red and IR current pulses and converts them into IR and red voltage pulses (IR and R), as shown in FIG. 8A, whose amplitudes represent the IR and red light intensity that would have been produced by the probe LEDs in the normal operation of the oximeter.

Figure 8B:
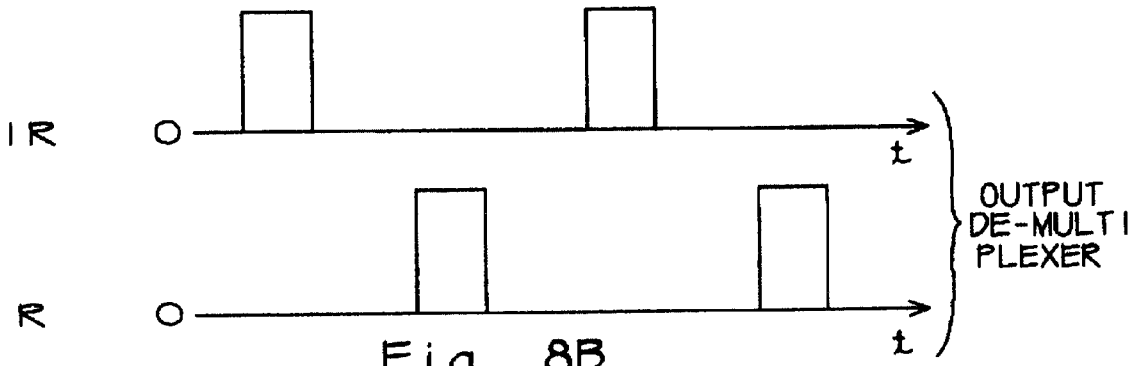

The $SpO_2$ simulator 100 (FIG. 8) also includes a de-multiplexer 172 which is connected to the output of the current sensor 170. In general, the polarity of the red and IR pulses from the oximeter's LED driver 34 is different, and thus the polarity of the voltage pulses (FIG. 8A) from the current sensor is different, for example, the IR pulses are positive and the red pulses are negative. The de-multiplexer detects this polarity and thus distinguishes between red and IR pulses and splits the red and IR voltage pulses into separate IR and red voltage pulse signals IR and R (FIG. 8B) and feeds these signals to a DC attenuator 174 from where they are transmitted to an AC modulator 176.

The attenuator and modulator 174/176 vary the IR and red pulse signals IR and R in accordance with values of parameters stored in databases in the memory of the microprocessor 104 and as displayed in the boxes 152, 154 and 156. This attenuation/modulation simulates what is caused by a real finger placed in the clamp 50 of the probe 28 and thus simulates $SpO_2$ levels, pulse rates and pulse amplitudes such as those occurring when the oximeter 24 is being used to monitor a patient.

Figure 8C:
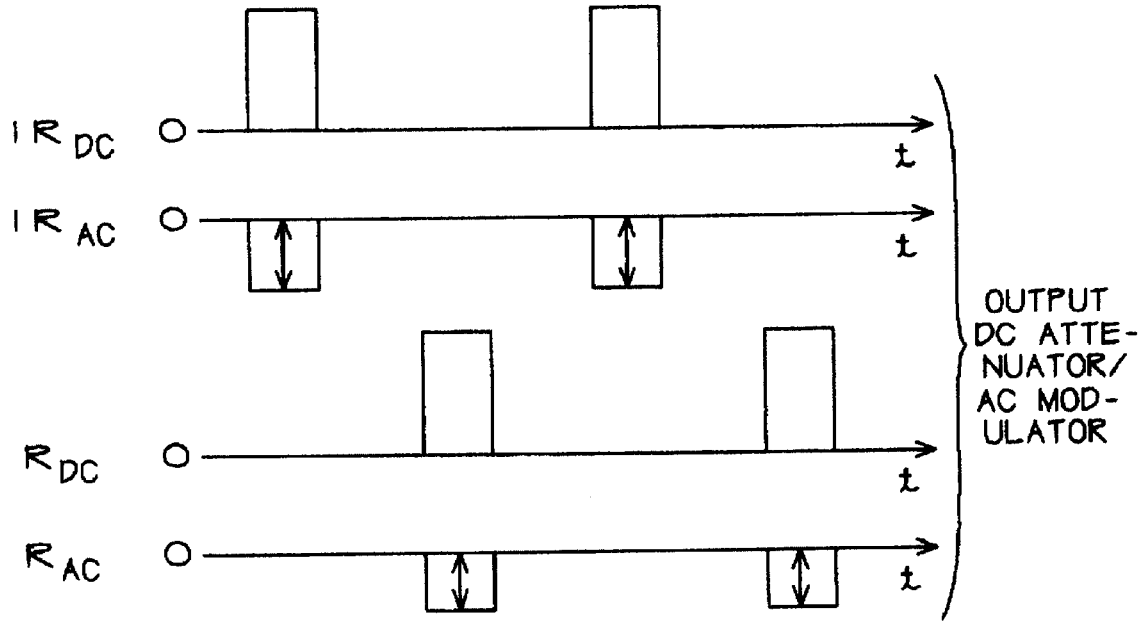

For example, the DC attenuator 174 under the control of the microprocessor 104 (FIG. 8) first modifies the IR and R pulse signals (FIG. 8B) from the de-multiplexer 172 to simulate the average component of the $SpO_2$ simulation, that is, constant physiological parameters caused by such factors as skin, bone and venous blood as attenuated by a human finger. The DC attenuator thus outputs $IR_{DC}$ and $R_{DC}$ voltage pulses, as shown in FIG. 8C, to the AC modulator 176 and to a weighting adder 178.

Mathematically, these pulses are defined as:

$$IR_{DC}=K_{IR}\times IR, \text{ and}$$

$$R_{DC}=KR\times R,$$

where IR and R represent the voltage levels of the IR and R pulse signals (FIG. 8B) from the de-multiplexer 172, and $K_{IR}$ and $K_R$ are the attenuation constants for IR and red signals respectively. Next, the AC modulator 176 under the control of the microprocessor 104 (FIG. 8), modifies the $IR_{DC}$ and $R_{DC}$ pulse signals (FIG. 8C—the arrows indicating modulation) from the DC attenuator 174 to simulate the pulsatile or variable component of the $SpO_2$ simulation. This pulsatile component is the variable physiological parameter of arterial blood, i.e., the pulse, as attenuated by a human finger, and as represented by the waveforms shown in FIGS. 8E and 8F which are based on Pleth diagrams of arterial blood flow. The information represented by these waveforms is stored in the memory of the microprocessor and relates to the well known R-curves which give the relationship between the R/IR ratios and $SPO_2$ values. A user of the testing apparatus selects an R curve and in so doing selects the waveforms of FIGS. 8E and 8F to be used.

Figure 8D:
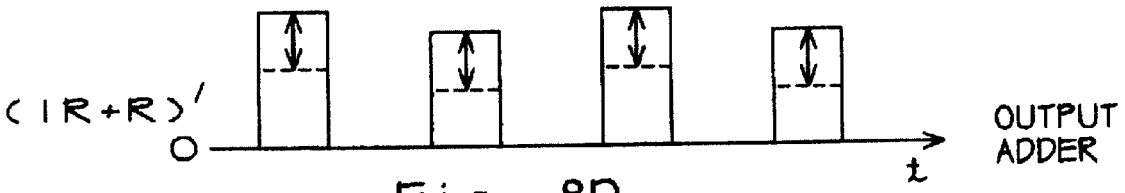
Figure 8E:
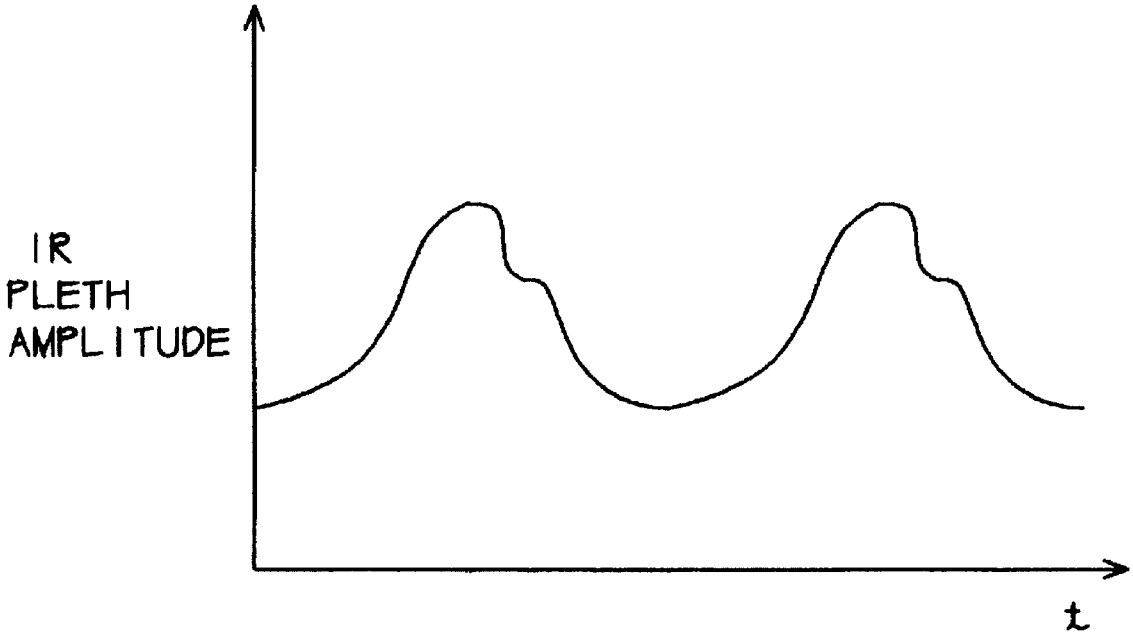
Figure 8F:
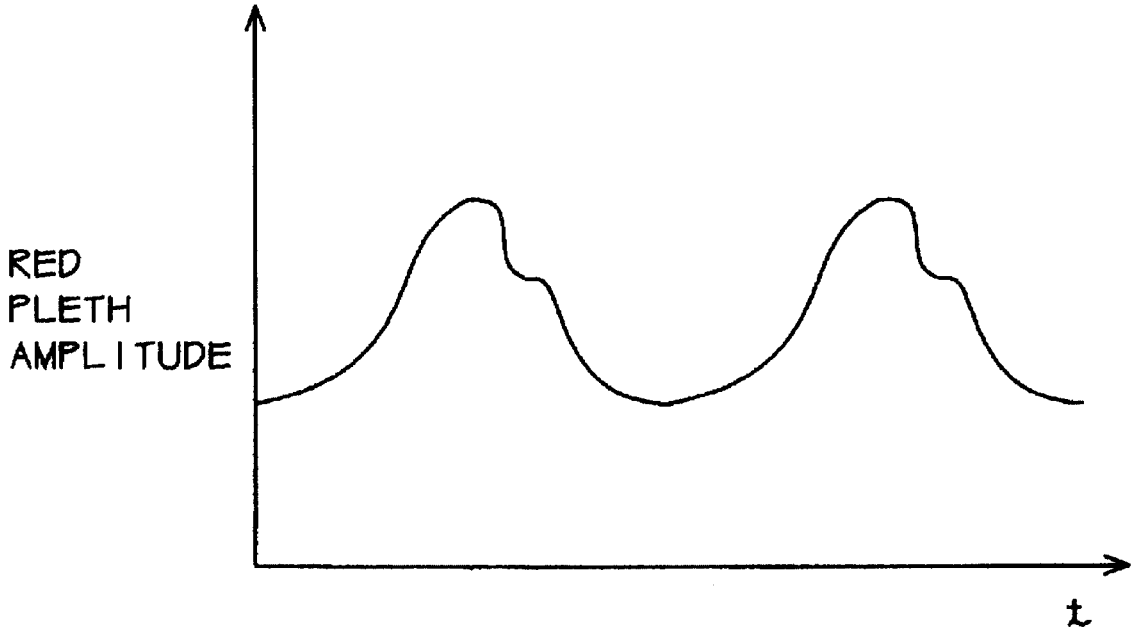

The AC modulator 176 (FIG. 8) outputs $IR_{AC}$ and $R_{AC}$ voltage pulse signals, as shown in FIG. 8C, to the weighting adder 178. These signals are mathematically defined as:

$$IR_{AC}=IR_{DC}\times IR_{PLETH(t)}, \text{ and}$$

$$R_{AC}=R_{DC}\times R_{PLETH(t)},$$

where $IR_{DC}$ and $R_{DC}$ are calculated as indicated above and $IR_{PLETH(t)}$ and $R_{PLETH(t)}$ are samples taken at predetermined intervals, preferably 5 msec in the preferred embodiment, from the Pleth waveforms of FIGS. 8E and 8F which, as stated, are stored in the memory of the microprocessor.

As referred to above, the $SpO_2$ simulator 100 (FIG. 8) includes the weighting or scaling adder 178 which receives the four output signals $IR_{DC}$, $IR_{AC}$, $R_{DC}$, and $R_{AC}$ (FIG. 8C) from the DC attenuator 174 and the AC modulator 176 and recombines these signals into attenuated and modulated IR and red voltage pulse signals (IR+R)', as shown in FIG. 8D, the arrows indicating modulation. In so doing, the adder also applies weighting or scaling factors to the $IR_{DC}$, $IR_{AC}$, $R_{DC}$, and $R_{AC}$ voltage pulse signals. In the disclosed embodiment, these weighting factors are 1 for $IR_{DC}$ and $R_{DC}$ and 0.20 for $IR_{AC}$ and $R_{AC}$. That is, the level of the $IR_{AC}$ and $R_{AC}$ signals is reduced to ⅕th of the level of the $IR_{DC}$ and $R_{DC}$ signals. The output of the weighting adder is mathematically defined as:

$$\text{Adder Output}=IR_{DC}+\tfrac{1}{5}IR_{AC}+R_{DC}+\tfrac{1}{5}R_{AC}.$$

The output of the weighting adder 178 is fed to a current driver 180 that converts the modulated IR and red voltage pulse signals (FIG. 8D) into modulated IR and red current pulse signals. These current pulse signals are conducted to the photodiode preamplifier 48 by the simulator adapter cable 92 and then to the signal processor 32 and the displays 38 and 40 of the pulse oximeter 24. The modulated IR and red current pulse signals are thus processed by the signal processor 32 just as if the current pulse signals had come from the photodiode 58 as a result of the probe 28 being attached to a real finger.

It is emphasized that the interface between the pulse oximeter 24 and the oximeter tester 20 is an electrical interface, with no optics involved. That is, the LED driver 34 and the current sensor 170 and the photodiode preamplifier 48 and the current driver 180, respectively, are electrically interconnected by the simulator adapter cable 92. At this time, the probe 28 is disconnected from the oximeter and is not involved in the testing of the oximeter's ability to process detected signals and to display accurate $SpO_2$ and pulse measurements.

The probe 28, having been disconnected from the pulse oximeter 24 to allow electrical testing of the oximeter's signal processing capabilities, is subjected to its own test by the probe analyzer 102 (FIGS. 8–15). The probe analyzer is part of the electronic testing system 90 of the subject testing apparatus 20 and operates under the control of the microprocessor 104 and the user interface 106. The probe analyzer tests the continuity of the probe circuits and the sensitivity of the probe optics. Continuity testing is described below with particular reference to FIGS. 5, 9, 13 and 14, and sensitivity testing is described below with particular reference to FIGS. 5, 10, 10A, and 15.

Considering continuity testing first, the probe analyzer 102 (FIGS. 8 and 9) includes LED and photodiode continuity current sources 181 and 182 which are connected to certain terminals in the interface connectors 114 and 116. When the probe connector 62 is connected to its matching interface connector 114 or 116, the continuity current sources are respectively connected to the LED and photodiode circuits through the conductors 64 and 68, respectively, at terminals 2, 3 and 5, 9 FIGS. 4 and 5 to supply testing current to these circuits and thereby to generate continuity testing voltages across the LEDs 54, 56 and the photodiode 58. The probe analyzer also includes a multiplexer 184 which receives the separate LED and photodiode continuity voltages, combines them into a single voltage signal with alternating LED and photodiode pulses, and feeds the combined signal to an analog-to-digital converter 186. The A/D converter transforms the signal into a series of discrete voltage pulses representative of the alternating LED and photodiode continuity voltages.

Figure 9:
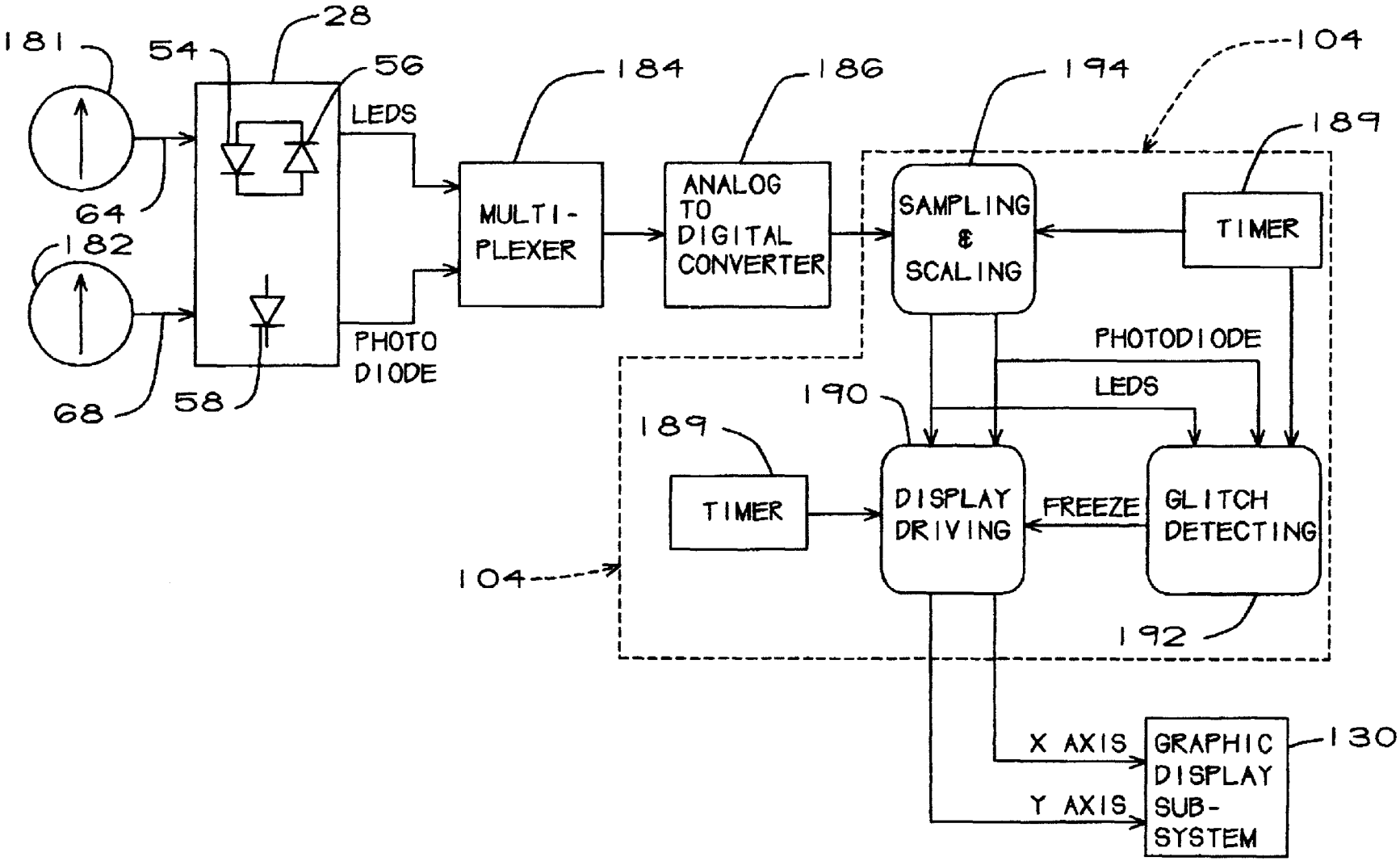
FIG. 9 is a functional block diagram of the continuity testing section of the probe analyzer of the subject testing apparatus, the probe analyzer being shown connected to the probe LEDs and photodiode, it being noted in this Fig. and other Figs. herein that the diagram boxes with square corners indicate functions implemented in hardware, whereas the boxes with rounded corners indicate functions implemented in software.

With continued reference to FIG. 9 in addition to FIGS. 13 and 14, the microprocessor 104 circuitry includes a timer 189 which, in general, generates clocking signals which call upon and cause various sub-routines to be executed. For probe 28 continuity testing, the timer executes the following software sub-routines: display driving 190 (including sweep generation), glitch or spike detecting 192, and sampling and scaling 194. The timer provides hardware interrupts of preferably from 1 to 5 milliseconds during which it executes the above-stated and subsequently described service routines. The display driving routine activates the x-axis of the LCD display screen 132 to provide horizontal sweep or time lines 196 and 198 (FIGS. 13 and 14) in the upper and lower channels at the "Good" level. The sampling and scaling routine samples and scales the output of the A/D converter 186 at predetermined time intervals, and the display driving routine applies these signal samples to the display screen.

More specifically, the display driving routine 190 applies signal samples representative of the continuity voltages from the LED circuit 54, 56, 64 to the y-axis in upper LED channel 160 and signal samples representative of the continuity voltages from the photodiode circuit 58, 68 to the y-axis in lower photodiode channel 162. The glitch detecting routine 192 senses when a glitch or spike of a predetermined threshold is sampled by the sampling and scaling routine and causes the display driving routine to freeze the display on the screen, as more fully described below.

Figure 10:
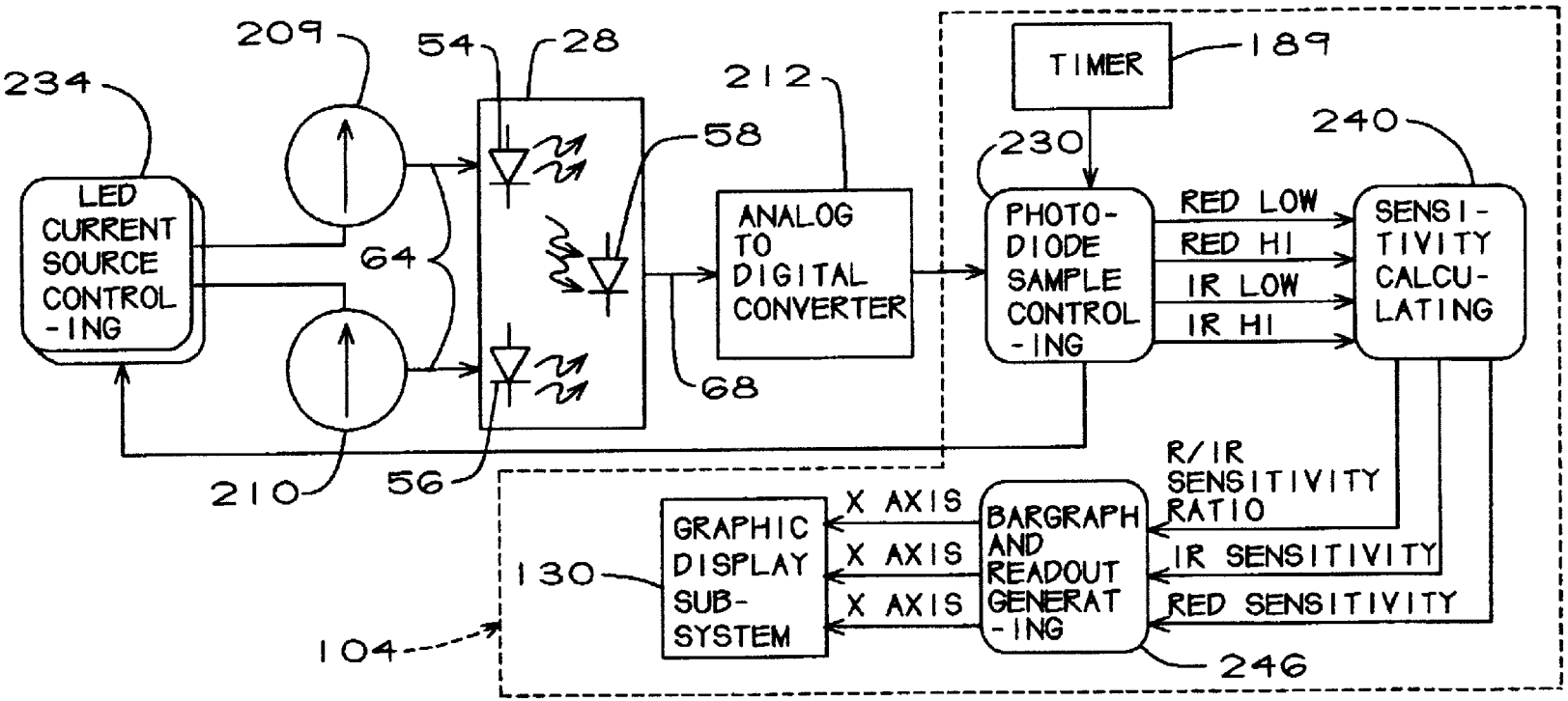
FIG. 10 is a functional block diagram of the sensitivity testing section of the probe analyzer, the probe analyzer being shown connected to the probe LEDs and photodiode.

Reference is now made to FIGS. 5, 8, 10, 10A and 15 for a description the probe sensitivity testing features of the probe analyzer 102 (FIG. 8). As shown in FIG. 10, the probe analyzer includes red and IR sensitivity current sources 209 and 210 respectively connected to the red and IR LEDs 54 and 56. These current sources are connected to certain terminals in the interface connectors 114 and 116 so that when the probe connector 62 is connected to its matching interface connector, the sensitivity current sources are connected to their corresponding red and IR LEDs.

The red and IR LEDs 54 and 56 are alternately activated by these current sources 209 and 210 (FIGS. 5 and 10) to produce red and IR light flashes. These flashes activate the photodiode 58 to generate a voltage signal across the photodiode having alternating red and IR pulses. The probe analyzer also includes an analog-to-digital converter 212 which receives the voltage signal from the photodiode 58 and transforms the signal into a series of discrete voltage pulses representative of the alternating red and IR sensitivity voltages.

Referring to FIGS. 10 and 15, for probe 28 sensitivity testing, the timer 189 of the microprocessor 104 executes the following software routines: photodiode sample controlling 230, LED current source controlling 234, sensitivity calculating 240, and bargraph and readout generating 246. The photodiode sample controlling routine activates the LED current source controlling routine alternately to apply current to the red and IR LEDs. The sample controlling routine also samples the IR and red pulses from the A/D converter 212 and develops red (R) low and red (R) high pulses and IR low and IR high pulses.

From the pulses developed by the photodiode sample controlling routine 230 (FIG. 10), the sensitivity calculating routine 240 generates a red sensitivity pulse from the red low and red high pulses, an IR sensitivity pulse from the IR low and IR high pulses, and an R/IR sensitivity ratio pulse from the red and IR sensitivity pulses. The bargraph and readout generating routine 246 applies the red sensitivity, the IR sensitivity and the R/IR sensitivity pulses to the x-axis of the LCD display screen in the upper, middle and lower bargraph channels 165, 166, and 168, respectively. Thus, horizontal bargraphs representative of the response of the photodiode 58 to the light flashes from the red and IR LEDs 54 and 56 are created.

DETAILED DESCRIPTION OF THE METHOD

Before describing the method for testing a pulse oximeter, as 24, according to the present invention, the status of the oximeter prior to the test, that is, the normal status of the oximeter is summarized, as shown in the lower part of FIG. 1. The probe connector 62 is normally connected to the preamp connector 46, as shown in phantom lines in FIG. 1, so that the probe clamp 50 is connected by the probe cable 30 and the preamp cable 42 to the main unit 26 of the oximeter. To monitor a patient, the probe clamp is clipped on the index finger of the patient whose $SpO_2$ level, pulse rate, and perhaps other parameters are to be checked. The oximeter is then turned on, causing the LEDs 54 and 56 to flash light at the finger and causing the photodiode 58 to receive the light that is transmitted through the finger.

To test the pulse oximeter 24 in accordance with the present invention, the first step is to disconnect the probe 28 (FIG. 1) from the oximeter's main unit 26. Specifically, the probe connector 62 is disconnected from the preamp connector 46, thus disconnecting the probe clamp 50 (including of course the LED and photodiode circuits) and the probe cable 30 from the main unit, shown in the center right in FIG. 1. At this point, the probe and the main oximeter unit are ready to be tested.

Hospital technicians often wish to test only the probe 28 (FIG. 1) center right including its cable 30, LEDs 54, 56 and photodiode 58, and not the oximeter 24 as a whole: They wish to confirm probe continuity and sensitivity, since the probe is often stored separately from the main unit 26 and is more likely to be defective than the remainder of the oximeter, as has been fully explained in the Background, above. Of course, it is also desirable and necessary to test the rest of the oximeter. The present method and apparatus readily enables such testing versatility. Thus, following disconnection of the probe connector 62 from the preamp connector 46, the next step of the method depends on what the technician wants to test: the main unit 26; the probe 28; or both.

To test the main unit 26, the plug 96 of the simulator adapter cable 92 is attached to the preamp connector 46, and the connector plug 95 is inserted into the interface connector 112. Testing is then continued as described below.

To test the probe 28, the probe connector 62 (FIG. 1) on the probe cable 30 is plugged into the interface connector, either 114 or 116, which matches the brand of oximeter 24 under test. It will be recalled that the testing apparatus is programmed to test various brands of oximeters having different probes 28, and an interface connector, as 114, 116, is provided for each brand to be accommodated. In the embodiment of the apparatus shown, however, only two brands, namely, brands X and Y, are capable of being tested since currently these two brands are the most commonly used. It will readily be understood, however, that the subject apparatus 20 could be modified to test additional brands without departing from the scope of the present invention.

To test both the probe 28 (FIG. 1) and the main unit 26 at the same time, the simulator adapter cable 92 and the probe cable 30 are both connected to the testing apparatus 20 in the manner described above. Even if only the probe or the main unit is to be tested to the exclusion of the other, both cables may be connected to the testing apparatus while either test is being conducted.

The description of the method of the present invention is continued now with a description of the steps for testing the main unit 26 (FIG. 1) and thereafter the steps for testing the probe 28. Using the keypad 136, the user turns on the testing apparatus 20 by pressing the on-off key O (FIG. 7) whereupon the electronic testing system 90 is activated and the default menu, that is the root menu, appears in the soft-key menu window 144 (FIG. 13). The testing apparatus as used to test the main unit is thereafter operated either in a basic manual mode or in a sequencing mode, the latter having both an automatic option and a manual option. The basic manual mode is first described.

TESTING THE MAIN UNIT 26—BASIC MANUAL MODE

In the basic manual mode, the technician first chooses individual values of $SpO_2$ percentage together with values of pulse rate and possibly pulse amplitude. To make this choice, the technician presses the hard keys M or P (FIG. 7) to select the $SpO_2$ submenu, as appears in FIG. 13. Then, using the keys F2 or F3, the $SpO_2$ display box 152 is selected, and with the keys F4 or F5, the desired value of $SpO_2$ percentage is set. Testing values of pulse rate and/or pulse amplitude, if desired, are similarly set and displayed in their respective boxes 154 and 156.

Next, the technician turns on the pulse oximeter 24, thereby causing the LED driver 34 (FIG. 8) alternately to generate IR and red current pulses which are directly fed to the current sensor 170 of the signal processor 100 of the testing apparatus 20. Again it is noted that these red and IR current pulses, in the normal operation of the pulse oximeter, would cause the red and IR LEDs in the probe 28 to flash. Since the probe 28 is disconnected from the oximeter 24, however, no such flashing occurs. Although believed understood, the fact that the probe may be connected to the testing apparatus at this time does not cause activation of the IR and red LEDs by the LED driver since the oximeter's normal connection of the LED driver to the probe is broken.

In response to the IR and red current pulses from the LED driver 34 (FIGS. 1, 8 and 8A) and as previously described, modulated IR and red i current pulse signals are generated by the signal processor 100 under control of the microprocessor 104. This modulated current represents the blood oxygen saturation ($SpO_2$) level, pulse rate, and pulse amplitude selected and displayed in the boxes 152, 154, and 156 (FIG. 13) and being used to test the oximeter 24. The modulated IR and red current is transmitted to the photodetector amplifier 48 (FIG. 8) by the simulator adapter cable 92 and is processed by the pulse oximeter just as if the current had come from the probe 28 attached to a real finger. The values of $SpO_2$ and pulse rate are read on the displays 38 and 40 of the pulse oximeter and compared with the settings displayed in boxes 152 and 154 of the display screen 132 to determine whether the oximeter is reading correctly.

TESTING THE MAIN UNIT 26—SEQUENCING MODE

Figure 11:
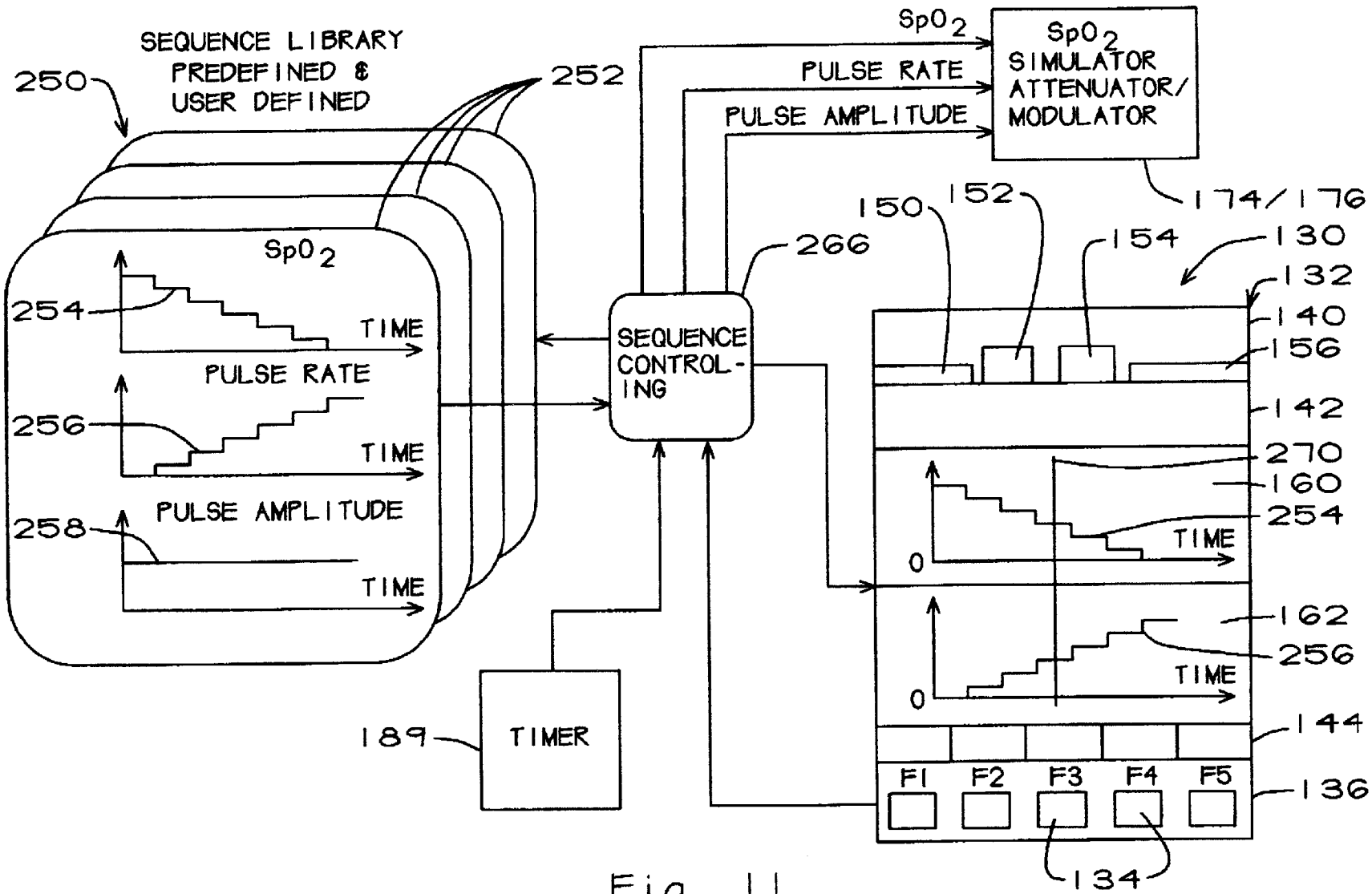
FIG. 11 is a functional block diagram and partially diagrammatic view of a sequencing feature of the subject testing apparatus.

In the sequencing mode of the testing apparatus 20, the subject method and apparatus test the pulse oximeter 24 with a sequence of programmed values of desired parameters ($SpO_2$ , pulse rate, and pulse amplitude in the disclosed embodiment). With reference to FIG. 11, the sequencing mode includes a library 250 of profiles or combinations 252 of parameters, each profile including a set of parameter curves, for example, $SpO_2$ curves, as 254: pulse rate curves, as 256; and pulse amplitude curves, as 258, all of which are loaded into the memory of the microprocessor 104. As suggested above, more or fewer parameters could be included if desired.

These profiles 252 are user-defined and preferably include both actual patient profiles from clinical studies and arbitrary, user-created profiles. The front profile diagrammatically illustrated in FIG. 11 is an arbitrary profile and includes an $SpO_2$ curve 254 declining in steps; a pulse rate curve 256 rising in steps, and a constant pulse amplitude curve 258. The patient profiles, not shown, typify the various conditions that are expected to be encountered in use of the oximeter, and for example, include constant values, that is, straight lines, like the pulse amplitude of FIG. 11, with intermittent deviations representative of physiological irregularities, such as desaturation dips, arrhytmia's, or the like deviations from the normal.

The sequencing mode (FIG. 11) can be operated either manually at an operator-controlled rate (the manual option) or automatically at a programmed rate (the automatic option). For this purpose, the timer 189 of the microprocessor 104 executes a sequence controlling sub-routine 266 which is initiated from the keypad 136. The sequence controlling subroutine feeds signals representing the selected profile data to the AC/DC modulators 174/176 of the $SpO_2$ simulator 100 (FIGS. 8 and 11) and to the graphic display subsystem 130 (FIGS. 8 and 11). In the disclosed embodiment, the sequence controlling routine feeds only the $SpO_2$ and pulse rate curves 254 to the upper and lower channels 160 and 162, respectively, of the display screen 132. Because of preferred space limitations on the display screen, the pulse amplitude curve 258 is not included, although it could be if desired.

Each profile 252 (FIG. 11) provides a cursor 270 (FIG. 12) which is contained in the memory of the microprocessor 104 as part of the profile data. The cursor is developed by the sequence controlling routine as a vertical sweep in the middle window 142 of the display screen 132 and its position at any given time corresponds with, that is, indicates on the curves, the values of the parameters being fed to the attenuator/modulator 174/176 and shown in the displays 152, 154, and 156. The cursor is programmed in memory to start at zero time base and to advance horizontally across the screen at timed intervals depending on whether the manual option or the automatic option is selected. If the manual option is selected, the cursor advances from one step to the next upon pressing one of the keys 134 and remains there until the key is pressed again, so the timing of the intervals is under the immediate control of the operator. If the automatic option is selected, the cursor advances from one step to the next at a rate programmed into the particular profile selected.

In use of the sequencing mode, the technician selects the desired profile 252 (FIG. 11) and the manual or automatic option with the keypad 136 and then turns on the pulse oximeter 24. As with the basic manual mode, the LED driver 34 (FIG. 8) alternately generates red and IR current pulses which are directly fed to the current sensor 170 of the signal processor 100 of the testing apparatus 20. The sequence controlling routine 266 feeds signals representing the profile data to the DC attenuator/AC modulator 174/176 and feeds the same profile signals plus the cursor signal to the graphic display subsystem 130. The modulated red and IR current is transmitted to the photodiode preamplifier 48 (FIG. 8) by the simulator adapter cable 92 and is processed by the pulse oximeter as in the basic manual mode.

TESTING THE MAIN UNIT 26—SEQUENCING MODE Manual or Interactive Option

In the manual, that is, interactive, option of the sequencing mode, the technician controls the advance of the cursor 270 across the screen 132 by pressing the appropriate key 134 of the keypad 136 each time the technician elects to step to the next set of values in the profile 252 selected. After each advance of the cursor, the technician compares the values of $SpO_2$, pulse rate, and pulse amplitude at the location of the cursor, which are being fed to the oximeter 24 and which are displayed in the display boxes 152, 156, and 158, with the readings on the displays 38 and 40 of the oximeter. Additionally, the technician may keep a datalog of the test by entering the values read on the oximeter's displays into the memory of the microprocessor 104 by pressing appropriate keys 134. Subsequently or at the same time, the test results stored in memory can be printed-out by connecting a printer 280 to the printer port 122 (FIG. 12).

TESTING THE MAIN UNIT 26—SEQUENCING MODE

Automatic Option

The automatic option of the sequencing mode allows two types of tests especially useful for testing pulse oximeters, as 24, namely a sweep test and a trend test. In the sweep test, a sequencing profile 252 is selected and the automatic sequencing mode is activated with the keypad 136 causing the cursor 270 to sweep in steps across the screen automatically from one value to the next and at a predetermined rate, preferably from about four to thirty seconds intervals but slower or faster is of course possible, as controlled by the timer 189. The interval depends on the characteristics of the oximeter, e.g., the specified amount of delay time needed by the oximeter to process and display the readings after each successive input, and as explained above, is built into the profile. Thus, the ability of the oximeter to respond within the delay time specified by the oximeter manufacturer can be tested. The results of the test are logged by connecting a cable 282 (FIG. 12) from the oximeter to the serial port 120 of the main unit 80 of the testing apparatus 20 whereby the readings on the oximeter's displays are fed into the memory of the microprocessor 104. Thereafter or simultaneously, and as described above, these results can be printed by connecting the printer 280 to the printer port 122.

The trend test is similar to the sweep test except that the intervals between each stepped advance of the cursor 270 are much longer, so that one complete cycle through the profile, as 254, i.e., one pass across the screen, may be as long as an hour or more. Here, it is first to be understood that certain pulse oximeters, as 24, have the capability of running trend tests on patients. For a trend test on a patient, the oximeter is connected to the patient and readings are taken and recorded over an extended period, up to an hour or more, to determine if there is a trend in the patient's condition. Thus, it is desirable to test the trend-taking capabilities of the oximeter. The subject method and apparatus 20 allow such a test.

To conduct a trend test on the oximeter 24, a patient profile 252 that incorporates parameters having deviations that show a trend is preferably selected. Alternatively, an arbitrary profile with a built-in trend may be selected. For example, the profile might include an $SpO_2$ curve that is essentially flat but has momentary desaturation dips which increase over time. The purpose of the trend test is to determine if the oximeter can detect these momentary dips and the trend thereof accurately.

In summary of the testing of the main unit 26, it is again emphasized that the optical interface of the pulse oximeter 24 is changed to an electrical interface. There is a direct electrical connection between the LED driver 34 and the current sensor 130 and a direct electrical connection between the current driver 142 and the photodiode amplifier 48. The probe 28 is out of the loop. Since the electrical interface of the subject testing apparatus bypasses the probe, the probe is not involved in the test of the oximeter's signal processor 32, LED driver 34, displays 38, 40, and photodiode amplifier 48.

TESTING THE PROBE 28—CONTINUITY TEST

The analysis of the probe 28 usually starts with a continuity test since field experience shows that the majority of probe defects are caused by frayed wires in the probe cable 30, many of which are intermittent defects. The testing apparatus 20 is turned on by pressing the on-off key 146. Then, the keys M or P are pressed to select the probe continuity sub-menu, as shown in FIGS. 13 and 14, thereby to display the continuity signals on the screen 132. The continuity current sources 181 and 182 (FIG. 9) deliver current to the LED and photodiode circuits while the probe cable is manually wiggled back and forth by the technician in an effort to reveal intermittent defects in the conductors 64 and 68.

Specifically, current of about 0.5 ma is sent through the conductors 64 and just one of the LEDs, as 54 (FIG. 9), by the current source 181. In the normal operation of the red and IR LEDs 54 and 56 as part of the pulse oximeter 24, current is caused to flow first in one direction and then in the other through the conductors 64, thereby alternately to excite the LEDs. For this continuity test, however, only one of the LEDs is excited since the principle objective is to check the continuity of the conductors where defects are more likely to occur.

The other continuity current source 182 (FIGS. 2–5 and 9) supplies a relatively low amperage current It, for example 0.5 ma, through the conductors 68 and the photodiode 58 (FIG. 5). It is significant here, and a feature of this invention, that the continuity current It flows through the photodiode in the opposite direction, as indicated by the arrow in FIG. 5, from the direction in which current flows when the photodiode is excited by flashes of light. This is a very practical feature since it causes the photodiode continuity signal, which would ordinarily be sensitive to ambient light, to be completely unresponsive to light. In this manner, the probe 24 and cable 30 can be freely wiggled during the test without any chance of artifact resulting from light sensitivity.

As shown in FIG. 9, and as previously described and under the control of the timer 189, the LED and photodiode voltage samples are applied by the display driving routine 190 of the microprocessor 104 to the y-axes of the LED and photodiode channels 160 and 162 of the display screen 132. In a properly functioning probe 30, there are no opens or shorts in the LED or photodiode circuits, so no voltage spikes or glitches will be developed, thereby causing the waveforms of the horizontal sweeps to be in the middle of their channels 160 and 162, that is, along the levels marked "Good," as shown in FIG. 13. If either circuit has a discontinuity, that is, a broken conductor or wire, as 64 or 68, a positive voltage sample, that is representing a glitch, will be fed to the screen 160 and the waveform will rise to the position marked "Open," such as shown in FIG. 14 with regard to the circuit for the photodiode 58. Similarly, although not shown, if the circuit is shorted, a negative sample also representing a glitch will be delivered to the screen, causing the waveform to drop to the position marked "Short."

What makes the probe continuity test according to the present invention so valuable is its ability to detect intermittent opens and shorts in the probe's red/IR circuit 54, 56, 64 and the probe's photodiode circuit 58, 68 (FIG. 5). A simple static test of probe continuity, such as a numeric display from a digital multi-meter, is not able to detect these open or short circuit conditions referred to as glitches that are characteristic of intermittently defective probes 24 and particularly the probe cables 30. The subject testing apparatus 20 provides simultaneous waveform displays of both the red/IR circuit and the photodiode circuit so that a single mechanical, i.e., manual, stress test, or wiggle test, of the probe cable will reveal any intermittent opens or shorts. In addition, any time a glitch is detected by the subject apparatus, the waveforms are frozen on the screen, as more fully described below, thereby eliminating any chance that the operator may overlook a glitch.

In the probe continuity testing mode, with the continuity sub-menu displayed as shown in FIG. 14, the soft key F3 toggles between an auto trigger mode and a glitch trigger mode. In the auto trigger mode, which is the typical operating mode, the waveforms (FIGS. 14) sweep continuously across the screen 132 until a glitch is detected. With reference to FIG. 9, when the glitch detecting routine 192 detects a glitch, it sends a signal to the display driving routine that causes the waveform, as 198 (FIG. 14), to freeze on the screen at the end of the current sweep across the screen. This captures or freezes the glitch waveform on the screen so that it can not be missed by the technician.

By toggling the key F3 into the glitch trigger mode, with the display screen 132 showing the probe continuity sub-menu (FIG. 14), the waveforms 196 and 198 do not sweep across the screen until a glitch is detected. This provides for maximum amount of glitch signature or pattern on the screen and allows the technician an opportunity carefully to examine the glitch. Another key F5 is used to clear the screen after a glitch has been detected and froze and to re-enable continuous waveform sweeping.

TESTING THE PROBE 28—SENSITIVITY TEST

If the probe 28 tests "Good" for continuity, it is next subjected to the probe sensitivity test to evaluate the IR and red optical performance of the probe. By pressing the hard keys M or P, the probe sensitivity sub-menu is selected, as shown in FIG. 15. The probe sensitivity test provides a quantitative method of evaluating the probe's red, IR and red/IR ratio optical performances. It is important to test this ratio because the ratio has a direct bearing on how the oximeter works. If there is too much or too little red (or too much or too little IR), there will be an imbalance so the signal to noise ratio will be compromised and an inaccurate reading will result.

Figure 10A:
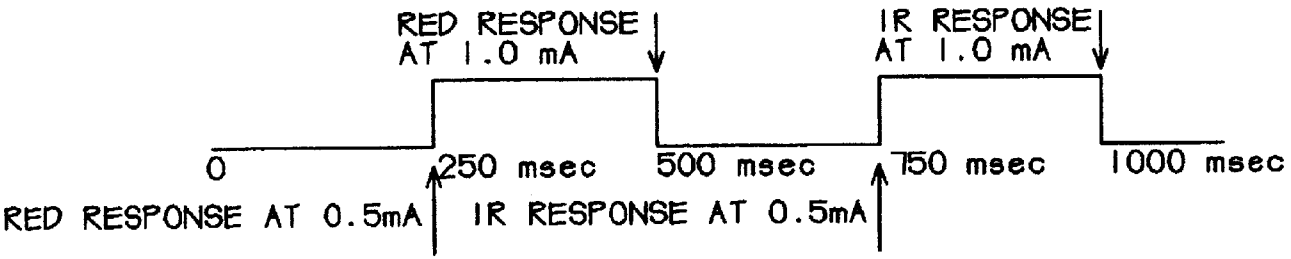
FIG. 10A is a photodiode waveform occurring in the circuit of FIG. 10.

With reference to FIGS. 10, 10A and 15, the bargraph and readout generating routine 246 provides horizontal bargraphs, as 300, in the bargraph channels 165, 166, and 168, together with corresponding numerical readouts at the ends of the bargraph channels. These bargraphs and readouts occur in response to activation of the LEDs 54, 56 by the sensitivity current sources 209 and 210 which in turn activate the photodiode 58. The bargraphs and readouts provide three measures of probe sensitivity, namely, (a) red channel sensitivity, i.e., the sensitivity of the photodiode to red light flashes; (b) IR channel sensitivity, i.e., the sensitivity of the photodiode to IR light flashes; and (c) the red/IR ratio sensitivity. The formulas for these sensitivities are:

(a) red channel sensitivity=[red response @ 1 mA]–[red response @ 0.5 mA]

(b) IR channel sensitivity=[IR response @ 1 mA]–[IR response @ 0.5 mA]

(c) red/IR ratio sensitivity=red sensitivity/IR sensitivity, where red response @ x mA is the response of the photodiode when the red LED is energized with x mA of current, and IR response @ x mA is the response of the photodiode when the IR LED is energized with x mA of current.

Based on the foregoing formulas, the photodiode sample controlling routine 320 (FIG. 10) measures four photodiode responses, which are taken across the photodiode 58 by the A/D converter and fed to the sample controlling routine 230 as digital pulses, so that in effect, the sample controlling routine is sampling the output of the photodiode. These four responses are: [red response @ 1 mA], [red response @ 0.5 mA], [IR response @ 1 mA], and [IR response @ 0.5 mA]. From these responses, the sample controlling routine produces the waveform shown in FIG. 10A, which also shows when the four responses are sampled. The sample controlling routine produces this waveform using the method set forth in the following paragraph.

First, under the control of the timer 189, the sample controlling routine 230 (FIG. 10) through the current source controlling routine 234 completely de-energizes the IR LED 56 by turning off the sensitivity current source 210, and energizes the red LED 54 by turning on its current source 209 with 0.5 mA. After a two hundred and fifty millisecond delay decremented by the timer, the controlling routine 230 samples the photodiode 58 output to yield the quantity "[red response @ 0.5 mA]." Secondly, the sample controlling routine 230, together with the source controlling routine 234, while maintaining the red LED de-energized, energizes the red LED with 1.0 mA, and after another two hundred and fifty millisecond delay, samples the photodiode output to yield the quantity "[red response @ 1.0 mA]."

Thirdly, the sample controlling routine 230 completely de-energizes the red LED 54 (FIG. 11) by turning off its sensitivity current source 209 through the source controlling routine 234 and energizes the IR LED 56 with 0.5 mA by turning on its current source 210 with the source controlling routine. After the timer decrements another two hundred and fifty millisecond delay (FIG. 12), the controlling routine 230 samples the photodiode output to yield the quantity "[IR response @ 0.5 mA]." Fourth, while keeping the red LED de-energized, the controlling routines 230/234 energize the IR LED with 1.0 mA by turning on its current source, and after another two hundred and fifty millisecond delay, the controlling routine 230 samples the photodiode output to yield the quantity "[IR response @ 1.0 mA]." The timer 189 causes this four-phase cycle to repeat once a second.

The photodiode waveform (FIG. 10A) produced by the sample controlling routine 230 in accordance with the methodology described above is thus available for the sensitivity calculating routine 240 (FIG. 10) to develop the red sensitivity, the IR sensitivity and the red/IR sensitivity ratio signals. The bargraph and readout generating routine 246 activates the x-axis of the display screen 132 with the red sensitivity, the IR sensitivity and the red/IR sensitivity ratio signals and creates red, IR, and red/IR bargraphs, as 300 (FIG. 15), respectively in the bargraph channels 165, 166, and 168. The generating routine also creates red, IR, and red/IR numerical readouts at the ends of the bargraphs, as also shown in FIG. 15.

The probe sensitivity test as described above measures the sensitivity at two different current levels and takes the difference which eliminates the effect of ambient light under normal lighting conditions. By contrast, a very primitive test of sensitivity would be to measure the output of the photodiode 58 when the LEDs 54 and 56 were driven with X amount of current and this output analyzed and assumed to represent the sensitivity of the components. However, this analysis would overlook the effect of ambient light. Even with no electrical drive on the LEDs, ambient light is always producing an output from the photodiode, so a simple pulsing of the LEDs would always represent the effect of both ambient light and the current source. By driving the LEDs with current at two different levels, and subtracting the outputs, the effect of ambient light is eliminated.

From the foregoing, it will be understood that the present method and apparatus 20 for testing pulse oximeters 24 provides many advantages. The fundamental concept of the subject invention is that the testing philosophy is based on an electrical interface between the oximeter and the testing apparatus, as contrasted with the optical interface heretofore utilized. Many advantages flow from this approach. Testing is more efficient and effective, safer and thus more reliable, because the biomedical technician can more readily determine whether a defect is in the main unit 26 of the oximeter or the probe 28. Bypassing the optical interface also has the advantage of not introducing error because of the need for perfect placement of an artificial finger in the probe clamp 50 of a pulse oximeter 24.

With the subject testing apparatus 20 electrically connected to a pulse oximeter, as 24, the oximeter delivers signals to the testing apparatus which would normally be delivered to the probe 28, and the testing apparatus modulates these signals in a manner which simulates the modulation resulting from a human finger placed in the probe when the oximeter is in regular use. The modulated signals are then fed back into the oximeter for processing by the oximeter and shown on its displays so that comparisons can be made with the known testing values. The subject method and apparatus allows for testing with single values of the testing parameters or with sequencing of profiles of the various parameters. Moreover, the test results can be manually or automatically logged and printed.

Experience of biomedical technicians in the patient care facilities shows that defects are usually in the probe 28, especially the probe cable 30. With the subject invention, it is possible to test the probe, that is, the probe probe cable and optics 54, 56 and 58, independently of the main unit 26 of the oximeter 24, whereas such testing has not been possible with the prior oximeter testing equipment. Also, since the probes are not unique to particular oximeters, they are often stored independently of the oximeter instruments, and sometimes in a manner which subjects them to undue stress, causing defects. In the past, technicians who have wanted to test only a probe which is separated from an oximeter instrument have had to search around the hospital for an instrument, connect the probe to the instrument, and then test them together just to determine whether the probe is functioning properly. The subject invention obviates this exercise since the subject testing apparatus can readily test the probe alone.

It is also to be noted that the apparatus of the present invention allows a technician to test the probe without the assistance of any other person since the multiple terminals 66, 70 of the probe connector are plugged into the interface connector 114 or 116 of the testing apparatus 20, and the testing is performed. If a technician, acting alone, were to attempt to test the continuity of the probe with a multimeter, it would be virtually impossible, or at least very impractical, to connect or contact the terminals of the probe connector with the prongs of the multimeter while simultaneously wiggling the cable and looking at the meter reading.

Still further, the subject method and apparatus 20 improves the integrity of testing of the oximeter because it improves the testing of the probe 28, and especially the probe cable 30, where a majority of the defects occur. This invention allows detection of intermittent opens and shorts in the probe cable, whereas previous testers might allow the oximeter to filter out spikes caused by such intermittent defects and thereby mask a developing problem. Still further, the subject method and apparatus displays the results of the testing with waveforms which can be carefully examined for a better analysis of the problems.

Although a preferred embodiment of the present invention has been shown and described, various modifications and substitutions may be made thereto without departing from the spirit and scope of the invention. Accordingly, it is to be understood that the present invention has been described by way of illustration and not limitation.

What is claimed is:

1. An apparatus for testing a pulse oximeter having means for optically sensing $SpO_2$ values of living tissue, electrical drive means for electrically activating the optically sensing means, and electrical signal processing means responsive to the optically sensing means for producing an oximeter signal corresponding to the $SpO_2$ value being sensed, said testing apparatus comprising:

first testing means bypassing the optically sensing means and responsive to the electrical drive means for generating selected first electrical test signals respectively representative of selected $SpO_2$ values in living tissue and for transmitting said first signals to the electrical signal processing means to test the ability of the signal processing means to process said representative $SpO_2$ values and produce oximeter signals corresponding to the selected $SpO_2$ values represented by the test signals generated, and second testing means for generating second electrical test signals, for transmitting the same to the optically sensing means, for receiving response signals from the optically sensing means in response to transmission of the second test signals, and for providing an indication of said response signals thereby to test the optically sensing means separately from said testing by the first testing means.

2. The apparatus of claim 1, wherein:

the optically sensing means includes an LED, a photodiode for producing an electrical output signal in response to activation of the LED, a first electrical circuit including the LED, and a second electrical circuit including the photodiode, said drive means being connected to the first electrical circuit for electrically activating the optically sensing means, said oximeter further including driven means interconnecting the second electrical circuit and the signal processing means for transmitting the electrical output signal from the photodiode to the signal processing means:

wherein said first testing means is capable of transmitting said first test signals instead of said photodiode output signal, to the driven means for testing the drive means, the driven means and the signal processing means, said second test signals including electrical continuity test signals and electrical sensitivity test signals, wherein said second testing means is capable of conducting the electrical continuity test signals through both of said first and second circuits to provide electrical continuity outputs, wherein said second testing means is capable of conducting the electrical sensitivity test signals through said first circuit to provide an electrical sensitivity output in the second circuit, and further including means for sensing said electrical continuity and sensitivity outputs from said circuits in response to said continuity and sensitivity test signals to test both the continuity and the optical sensitivity of the optical sensing means.

3. An apparatus for testing a pulse oximeter capable of sensing the $SpO_2$ in living tissue and including a probe including LEDs and a photodiode; and an electronic unit including an LED driver providing output signals for activating the LEDs, an electronic signal processor for receiving and processing input signals from the photodiode in response to activation of the LEDs, and a display for showing the $SpO_2$ values represented by the input signals, said probe releasably interconnecting the LED driver and the LEDs and the photodiode and the signal processor, comprising:

means operable with the probe disconnected from the LED driver and the signal processor for providing electrical test signals in response to output signals from the LED driver;

means for modulating said electrical test signals so as to provide modulated electrical test signals representative of selected $SpO_2$ values corresponding to those in living tissue; and means for transmitting said modulated electrical test signals to the signal processor in place of said input signals to cause the signal processor to process the test signals as if they were said input signals whereby $SpO_2$ values shown on the display can be compared with a range of selected $SpO_2$ values corresponding to the modulated electrical test signals thereby to test said electronic unit over its normal operating range.

4. The apparatus of claim 3, further including:

electronic memory means adapted to store an $SpO_2$ profile including a plurality of $SpO_2$ values which vary over a predetermined time base; and wherein said modulating means is adapted to modulate said electrical test signals with selected $SpO_2$ profiles so as to provide modulated electrical test signals representative of selected $SpO_2$ profiles.

5. The apparatus of claim 4 further including:

display means;

wherein said electronic memory means is also adapted to store a cursor for said profiles, wherein said modulating means is further adapted to feed a selected $SpO_2$ profile and said cursor to said display means so that a selected profile and cursor can be displayed, wherein said memory means, said modulating means and said display means cooperate to cause the cursor to move in steps over the displayed profile at a predetermined rate stored in said memory, with the position of the cursor at each step indicating on the display means the value of $SpO_2$ then modulating the test signal whereby the oximeter can be tested with said profile of $SpO_2$ values sequentially delivered to the signal processor.

6. An apparatus for testing the probe of a pulse oximeter having an electronic unit including an LED driver and an electronic signal processor; said probe including red and IR LEDs, a photodiode, and a probe cable, said probe cable being releasably connected to the driver and the signal processor when the probe is being used to sense the $SpO_2$ of living tissue and to feed a signal representative of the same to the signal processor, comprising:

means for supplying current to the LEDs and the photodiode while the probe is disconnected from the driver and the signal processor to provide electrical continuity outputs from the LEDs and the photodiode;

means for driving the LEDs while the probe is disconnected from the driver and the signal processor so as to activate the photodiode and provide electrical sensitivity outputs from the photodiode; and means for sensing said outputs thereby to indicate the sensitivity and the continuity of the probe.

7. An apparatus for testing a pulse oximeter probe which includes optical sensing means providing an LED circuit including red and IR LEDs and a photodiode circuit including a photodiode, there being an interactive red LED-photodiode combination and an interactive IR LED-photodiode combination, said LED circuit, said photodiode circuit, said interactive red LED-photodiode combination, and said interactive IR LED-photodiode combination constituting first, second, third, and fourth parts, respectively, of the optical sensing means capable of being tested for continuity and sensitivity, comprising:

current supply means simultaneously connectable to the LED and photodiode circuits for causing testing current to flow in at least one of said circuits and for producing test output signals representative of the test results on at least one of said parts of the optical sensing means; and means for receiving the test output signals and being responsive to the magnitude thereof to produce an indication of the results of said test to a user of the apparatus.

8. The apparatus of claim 7, further including: indicator means, wherein said current supply means and said receiving means interact to produce test output signals each of which individually represents the test results for one of said parts of the optical sensing means, and wherein said indicator means is capable of indicating each of said individual output signals, whereby selected parts of the optical sensing means can be separately analyzed.

9. The apparatus of claim 7, further including:

indicator means;

wherein for said continuity test, the current supply means is adapted to supply current simultaneously to each of said circuits thereby to produce LED circuit continuity output test signals and photodiode circuit continuity output test signals;

wherein said receiving means includes means for multiplexing said continuity output test signals and means for feeding said multiplexed output test signals to said indicator means; and wherein said indicator means is adapted separately to indicate the LED and photodiode continuity output signals thereby to enable individual analysis of the continuity of the LED and photodiode circuits.

10. The apparatus of claim 7, further including:

indicator means;

wherein said receiving means includes microprocessor means;

wherein, for said sensitivity test, the microprocessor means is adapted to cause the current supply means to alternately supply current to the red LED and the IR LED whereby said test output signals are alternately red sensitivity signals and IR sensitivity signals, said microprocessor means being adapted to develop red sensitivity/IR sensitivity ratio signals from said red and IR sensitivity signals, and said indicator means being adapted to indicate said red sensitivity signals, said IR sensitivity signals, and said red sensitivity/IR sensitivity ratio signals to a user of the apparatus, thereby to enable the user to analyze the sensitivity of said third and fourth parts of the optical sensing means.

11. An apparatus for testing the continuity of a pulse oximeter probe which provides an LED circuit and a photodiode circuit, said apparatus comprising:

means for activating each of said circuits so as to produce an electrical test output in each circuit representative of whether the circuit is open, continuous or shorted;

means for separating the test outputs representing the LED circuit from the test outputs representing the photodiode circuit; and means for analyzing each of said outputs to determine whether or not the LED circuit or the photodiode circuit is open, continuous or shorted.

12. The apparatus of claim 11, wherein:

said activating means is adapted to activate said photodiode circuit by causing current to flow in a direction in said photodiode circuit opposite to the direction current flows when light activates the photodiode.

13. The apparatus of claim 11, wherein said analyzing means includes display means providing separate channels respectively associated with the test outputs of the LED and photodiode circuits, and wherein said analyzing means is capable of displaying representations of said test outputs in the respective channels for the LED and photodiode circuits so that a predetermined representation indicates whether the respective circuit is open, continuous, or shorted.

14. The apparatus of claim 11, wherein said analyzing means includes display means, wherein said analyzing means is capable of displaying representations of said test outputs on the display means so that a predetermined representation represents a circuit that is open, continuous, or shorted, and wherein said analyzing means is capable of freezing the representation on the display means when a circuit is open or shorted.

15. An apparatus for testing the sensitivity of a pulse oximeter probe which provides red and infrared LEDs an a photodiode adapted to be alternately activated by said LEDs, said apparatus comprising:

means for electrically alternately activating the LEDs so as to produce electrical red and IR sensitivity test output signals from the photodiode;

means for producing red sensitivity/IR sensitivity ratio signals from said red and IR test output signals; and means for indicating each of said red sensitivity, IR sensitivity and red sensitivity/IR sensitivity ratio signals to determine the sensitivity of the optical sensing means.

16. The apparatus of claim 15, wherein said activating means is adapted alternately to supply relatively low and relatively high current to the red and IR LEDs to produce alternately low and high red signals and low and high IR signals, said apparatus further including means for subtracting the low red from the high red signal and the low IR and from the high IR, and wherein said producing means is adapted to produce said red sensitivity signal from the difference between the high and low red signals and to produce said IR sensitivity signal from the difference between the high and low IR signals.

17. The apparatus of claim 15, wherein said indicating means includes display means for respectively separately displaying said red and IR sensitivities and said red sensitivity/IR sensitivity and said red sensitivity/IR sensitivity ratio.

18. A method for testing a pulse oximeter having means for optically sensing $SpO_2$ values in living tissue, means for electrically activating the optically sensing means, and electrical means responsive to the optically sensing means for indicating the $SpO_2$ value in tissue being sensed, said method comprising the steps of:

generating first test signals representative of $SpO_2$ values in living tissue in response to the electrically activating means and independently of the optically sensing means, transmitting the first test signals to the electrical responsive means independently of the optically sensing means to test the ability of the oximeter to indicate said representative $SpO_2$ values, generating a second test signal independently of the electrically activating means for testing the optically sensing means, transmitting the second test signal to the optically sensing means independently of the electrically activating means, and receiving an output from the optically sensing means indicative of the responses of the optically sensing means to the second test signal, thereby to test the operability of the optically sensing means.

19. The method of claim 18, wherein said generating step for testing the optically sensing means is capable of testing the electrical continuity of the optically sensing means.

20. The method of claim 18, including the further step of:

disconnecting the optically sensing means from the electrically activating means and the electrical responsive means, wherein said generating step includes receiving an output signal from the electrically activating means and modulating said output signal so as to provide a modulated test signal representative of a selected value of $SpO_2$ corresponding to that in living tissue; and wherein said transmitting step involves transmitting said modulated test signal to the electrical responsive means so as to provide a modulated test signal representative of a selected value of $SpO_2$ corresponding to that in living tissue.

21. A method for testing a pulse oximeter over a range of values of $SpO_2$ expected to exist in living tissue said oximeter having a probe including LEDs and a photodiode; and an electronic unit including an LED driver providing an output signal for activating the LEDs, an electronic signal processor for receiving and processing input signals from the photodiode representative of $SpO_2$ values in living tissue in response to activation of the LEDs, and a display for showing the $SpO_2$ values represented by the input signals, said probe releasably interconnecting the LED driver and the LEDs and the photodiode and the signal processor, comprising the steps of:

disconnecting the probe from the driver and signal processor;

generating an electrical test signal in response to the output signal from the LED driver;

modulating said electrical test signal so as to provide a modulated electrical test signals representative of selected $SpO_2$ values in living tissue;

transmitting said modulated electrical test signals to the signal processor in place of said input signals to cause the signal processor to process the test signals as if they were said input signals thereby to test said electronic unit and, displaying the selected $SpO_2$ values so that a comparison can be made with the $SpO_2$ values displayed by the oximeter display to determine the accuracy of the oximeter over a range of $SpO_2$ values.

22. The method of claim 21, including the further steps of:

electronically storing an $SpO_2$ profile including a plurality of $SpO_2$ values which vary over a predetermined time base; and wherein said modulating step is adapted to modulate said electrical test signals with selected $SpO_2$ profiles so as to provide modulated electrical test signals representative of selected $SpO_2$ profiles.

23. The method of claim 22 including the further steps of:

electronically storing a cursor for said profiles and a stepping rate for the cursor, displaying a selected profile and said cursor; and moving the cursor in steps over the displayed profile at said stepping rate so that the position of the cursor at each step indicates the value of $SpO_2$ then modulating the test signal whereby the oximeter can be tested with said profile of $SpO_2$ values sequentially delivered to the signal processor.

24. A method for testing a pulse oximeter probe which includes optical sensing means providing an LED circuit including red and IR LEDs and a photodiode circuit including a photodiode, there being an interactive red LED-photodiode combination and an interactive IR LED-photodiode combination, said LED circuit, said photodiode circuit, said interactive red LED-photodiode combination, and said interactive IR LED-photodiode combination constituting first, second, third, and fourth parts, respectively, of the optical sensing means one or more of which is capable of being tested for the parameters of continuity and sensitivity, comprising the steps of:

electrically activating said circuits so as to produce electrical test output signals which are representative of at least one of the parameters to-be-tested; and sensing the test output signals and displaying an indication of whether one or more of said parts meet the standards established for said at least one of the parameters to-be-tested.

25. The method of claim 24, wherein:

said activating step activates the circuits so as to produce output test signals which are not affected by ambient light on the photodiode.

26. The method of claim 24, wherein:

said activating step involves causing current to flow in the photodiode circuit in the opposite direction from that occurring when the photodiode is activated by light.

27. The method of claim 24, wherein:

said activating step involves alternatively supplying high and low current pulses in the red and IR LED circuits, respectively, to produce alternate red high and red low test output signals and IR high and IR low test output signals, said activating step further involving subtracting red low signals from the corresponding red high signals and IR low signals from the corresponding IR high signals, thereby to produce said red sensitivity and said IR sensitivity signals, respectively, and including the further step of generating red sensitivity/IR sensitivity ratio signals from said red sensitivity and said IR sensitivity signals, and wherein said sensing step involves analyzing said red and IR sensitivity signals and said red sensitivity/IR sensitivity ratio signals thereby to determine the sensitivity of the optically sensing means.

28. The method of claim 24, further including the step of:

displaying graphical representations of the test output signals sensed from said circuits thereby to indicate the condition of the continuity of said circuits, and displaying graphical representations of the test output signals sensed from the photodiode thereby to indicate the sensitivity of the optically sensing means.

29. A method for testing the continuity of a pulse oximeter probe which provides an LED circuit and a photodiode circuit, comprising the steps of:

activating each of said circuits so as to produce an electrical test output in each circuit representative of whether the circuit is open, continuous or shorted;

separating the test outputs representing the LED circuit from the test outputs representing the photodiode circuit; and analyzing each of said outputs to determine whether or not the LED circuit or the photodiode circuit is open, continuous or shorted.

30. The method of claim 29, wherein said analyzing step further includes:

displaying representations of said test outputs so that a predetermined representation represents a circuit that is open, continuous, or shorted, and freezing the representation when a circuit is open or shorted.

31. The apparatus of claim 1, wherein said first and second testing means are capable of independently but simultaneously testing the signal processing means and the optically sensing means.

32. The apparatus of claim 1, wherein there is a housing enclosing both the first and second testing means, and wherein there are spaced first and second connector means on the housing respectively connected to the first and second testing means and respectively adapted to be connected to the signal processing means and the optically sensing means.

33. The apparatus of claim 1, wherein there are microprocessor means for controlling the first and second testing means to enable the first and second testing means to test either the signal processing means or the optically sensing means separately or to test both the signal processing means and the sensing means simultaneously.

34. The apparatus of claim 1 wherein the optically sensing means includes an LED, a photodiode for producing an electrical output signal in response to activation of the LED, a first electrical circuit including the LED, and a second electrical circuit including the photodiode, said drive means being connected to the first electrical circuit for electrically activating the optically sensing means, said oximeter further including driven means interconnecting the second electrical circuit and the signal processing means for transmitting the electrical output signal from the photodiode to the signal processing means;

wherein said first testing means is capable of transmitting said first test signals, instead of said photodiode output signal, to the driven means for testing the drive means, the driven means and the signal processing means, wherein said second test signals are electrical continuity test signals, wherein said second testing means is capable of conducting the electrical continuity test signals respectively through said first and second circuits to provide electrical continuity outputs, and wherein there are means for sensing said electrical continuity outputs and displaying an indication of the continuity of the optical sensing means.

35. The apparatus of claim 1 wherein the optically sensing means includes an LED, a photodiode for producing an electrical output signal in response to activation of the LED, a first electrical circuit including the LED, and a second electrical circuit including the photodiode, said drive means being connected to the first electrical circuit for electrically activating the optically sensing means, said oximeter further including driven means interconnecting the second electrical circuit and the signal processing means for transmitting the electrical output signal from the photodiode to the signal processing means;

wherein said first testing means is capable of transmitting said first signals, instead of said photodiode output signal, to the driven means for testing the drive means, the driven means and the signal processing means, wherein said second test signals are electrical sensitivity test signals, wherein said second testing means is capable of conducting the electrical sensitivity test signals through said first circuit to provide electrical sensitivity outputs in the second circuit, and wherein there are means for sensing said electrical sensitivity outputs and displaying an indication of the optical sensitivity of the optical sensing means.

36. The apparatus of claim 3, wherein the apparatus includes means for displaying the values of $SpO_2$ represented by the modulated electrical test signals whereby $SpO_2$ values showing on the oximeter display can be compared with selected $SpO_2$ values showing on the displaying means thereby to determine the accuracy of the oximeter throughout a range of $SpO_2$ values.

37. An apparatus for testing the continuity of a pulse oximeter probe which provides LED and photodiode circuits connected to LED and photodiode terminals of a probe connector, said apparatus comprising:

means simultaneously connectable to the LED and photodiode terminals of the probe connector for activating each of said circuits so as to produce an electrical test output in each circuit representative of whether the circuit is open, continuous or shorted; and means responsive to said test outputs for displaying indicia representing whether said LED and photodiode circuits are open, continuous or shorted.

38. The apparatus of claim 37, wherein the activating means is a current source for each of said circuits.

39. The apparatus of claim 38, wherein the current sources are simultaneously connectable to their respective LED and photodiode circuits, and wherein the activating means causes current from the current sources to supply current simultaneously to said circuits.

40. The apparatus of claim 37, wherein the responsive means is capable of sensing and displaying intermittent test outputs of a predetermined threshold indicative of a glitch in either of said circuits.

41. The apparatus of claim 37, wherein there are means for combining the test outputs into a combined signal with alternating LED and photodiode pulses, and wherein there are means for using the LED and photodiode pulses to display an indication of whether the LED and photodiode circuits are open, continuous or shorted.

42. The apparatus of claim 41, wherein the combining means combines the test outputs into a combined analog signal with said alternating LED and photodiode pulses, wherein there are means for converting the combined analog signal into discrete digital signals representative of said LED and photodiode pulses; and wherein there are means for sampling the digital signals and displaying the same to indicate whether or not the LED circuit or the photodiode circuit is open, continuous or shorted.

43. An apparatus for testing the continuity of a pulse oximeter probe that has an LED circuit and a photodiode circuit, comprising means for supplying testing current to each of the LED and photodiode circuits to produce responses including separate analog LED and photodiode continuity voltages, means for combining said voltages into a single voltage signal with alternating LED and photodiode pulses, means for converting the single voltage signal into a series of discrete digital voltage pulses representative of the alternating LED and photodiode pulses, means for sampling the digital voltage pulses, display means, and means for activating the display means with the signal samples to indicate whether the LED and photodiode circuits are open, continuous, or shorted.

44. The apparatus of claim 15, wherein said indicating means includes display means for respectively displaying bargraphs in separate channels of said red and IR sensitivities and said red sensitivity/IR sensitivity ratio.

45. The method of claim 18, wherein said generating step for testing the optically sensing means is capable of testing the optical sensitivity of the optically sensing means.

46. The method of claim 19, wherein said generating step for testing the optically sensing means is capable of testing the optical sensitivity of the optically sensing means.

47. A method for testing a pulse oximeter probe which includes optical sensing means providing an LED circuit including red and IR LEDs and a photodiode circuit including a photodiode, there being an interactive red LED-photodiode combination and an interactive IR LED-photodiode combination said LED circuit, said photodiode circuit, said interactive red LED-photodiode combination, and said interactive IR LED-photodiode combination constituting first, second, third, and fourth parts, respectively, of the optical sensing means to be subjected to such testing including the parameters of continuity and sensitivity, comprising the steps of:

electrically activating said circuits so as to produce electrical test output signals which are representative of the parameters to-be-tested of said parts;

electrically separating the test output signals so that there is a test output signal representative of continuity for each of said first and second parts and a test output signal representative of the sensitivity for each of said third and fourth parts;

and analyzing each of said output signals to determine whether or not said parts meet the standards established for said parameters.

48. The method of claim 24 which involves the use of a testing device capable of performing said activating, sensing and displaying steps, further including the step of:

electrically connecting the testing device simultaneously to both the LED and photodiode circuits prior to said electrically activating step thereby to enable testing of selected ones of said parts.

49. A method for testing the continuity of a pulse oximeter probe that includes an LED circuit and a photodiode circuit, comprising the steps of:

simultaneously connecting electrical activating means to both of the LED and photodiode circuits, electrically activating each of said circuits with test signals thereby to produce an electrical test output in each circuit representative of whether the circuit is open, continuous or shorted; and processing the test outputs to provide a visual indication of whether or not each circuit is open, continuous or shorted.

50. The method of claim 49, wherein the activating step involves simultaneously supplying said test signals in the form of current fed to each of said circuits from separate current sources respectively associated with said circuits.

51. The method of claim 49 wherein the probe includes a probe cable including conductors that are part of said circuits, including the further step of:

moving the cable around during the electrical activating so that if one or more of the conductors has an open or short condition that occurs only intermittently, such movement will cause the open or short to occur.

52. The method of claim 51, wherein the moving step causes a voltage spike in said test output of the circuit in which an intermittent short or open condition exists;

and wherein the processing step is responsive to the voltage spike to provide a visual indication of the same, whereby such intermittent short or open conditions are not overlooked by the user performing the test.

53. A method for testing the continuity of a pulse oximeter probe that has an LED circuit and a photodiode circuit, comprising the steps of:

supplying current to both the LED and photodiode circuits to produce responses including separate LED and photodiode continuity voltages; sensing said responses and combining them into a single voltage signal with alternating LED and photodiode pulses;

converting the single voltage signal into a series of discrete voltage pulses representative of the alternating LED and photodiode pulses; and using the discrete voltage pulses to display indications of whether the LED and photodiode circuits are open, continuous or shorted.

*54. An apparatus for testing the sensitivity of a pulse oximeter probe which provides red and infrared LEDs and a photodiode, said apparatus comprising:*

*a red current source that generates red LED activating signals, applies them to the red LED, and generates red high and red low outputs on the photodiode;*

*an IR current source that generates IR LED activating signals, applies them to the IR LED, and generates IR high and IR low outputs on the photodiode;*

*sensor circuitry that is responsive to the red high and the red low outputs on the photodiode and to the IR high and the IR low outputs on the photodiode and that generates red testing signals and IR testing signals from said outputs; and*

*a display that is responsive to the red and IR testing signals and produces an indication thereof, said indication being an indication of the sensitivity of the probe.*

*55. The apparatus of claim 54,*

*wherein the red current source generates high and low red activating signals and applies them to the red LED thereby to produce said high and low red outputs in the photodiode; and*

*wherein the IR current source generates high and low IR activating signals and applies them to the IR LED thereby to produce said high and low IR outputs in the photodiode.*

*56. An apparatus for testing the sensitivity of a pulse oximeter probe which provides red and infrared LEDs and a photodiode, said apparatus comprising:*

*means for applying red high and red low LED activating signals to the red LED so that red high and red low outputs are on the photodiode;*

*means for applying IR high and IR low LED activating signals to the IR LED so that IR high and IR low outputs are on the photodiode;*

*means for sensing the outputs on the photodiode and producing a red testing signal from the red high and red low outputs on the photodiode and an IR testing signal from the IR high and IR low outputs on the photodiode, said red and IR testing signals being the differences between their respective high and low outputs; and*

*means for displaying an indication of said testing signals whereby said indication is an indication of the sensitivity of the probe.*

*57. A method for testing the sensitivity of a pulse oximeter probe which provides red and infrared LEDs and a photodiode, comprising the steps of:*

*activating one of the LEDs with signals of high and low amplitude thereby producing first high and low outputs on the photodiode;*

*sensing the first high and low outputs on the photodiode;*

*producing a first testing signal from said first high and low outputs;*

*activating the other of the LEDs with signals of high and low amplitude thereby producing second high and low outputs on the photodiode;*

*sensing the second high and low outputs on the photodiode;*

*producing a second testing signal from said second high and low outputs; and*

*displaying an indication of said first and second testing signals thereby to indicate the sensitivity of the probe.*

*58. The method of claim 57,*

*wherein producing the first and second testing signals involves obtaining the difference between the first high and low outputs and the difference between the second high and low outputs resulting respectively in first and second difference signals.*

*59. An oximeter tester for an oximeter that includes a signal processor, an LED driver and a probe including LED and photodiode circuits respectively including light emiting diodes and a photodiode, the probe being releasably connected to the signal processor and the LED driver, the tester comprising:*

*a first sensor having an input adapted to be connected to the LED driver in the oximeter in place of the probe, the first sensor, when so connected, receiving electrical red and IR drive signals from the LED driver of the oximeter and producing red and IR pulses,*

*a de-multiplexer coupled to the sensor and separating the red and IR pulses,*

*a source of $SpO_2$ waveforms corresponding to those normally received by the oximeter when its probe is attached to a human being,*

*a modulator coupled to the de-multiplexer and modulating the separate red and IR pulses with said $SpO_2$ waveforms from the source and thereby generating first electrical test signals representative of $SpO_2$ waveforms of living tissue corresponding to those normally received by the oximeter when its probe is attached to a human being,*

*a tester driver having an input coupled to the modulator and an output adapted to be connected to the signal processor in the oximeter and, when so connected, delivering said first electrical test signals to the signal processor thereby to test the ability of the signal processor to process said $SpO_2$ waveforms and produce oximeter read-outs corresponding to $SpO_2$ values represented by the test signals generated;*

*a current source adapted to be connected to one or more diodes in the probe and, when so connected, coupling second electrical test signals to said one or more of the diodes thereby to activate the one or more diodes;*

*a second sensor adapted to be connected to one or more diodes in the probe and, when so connected, receiving response signals from said one or more of the diodes in response to the second electrical test signals;*

*a display;*

*circuitry interconnecting the second sensor and the display and applying signals to the display indicative of the response signals from the second sensor; and*

*a microprocessor coupled to the modulator, the display and the source and controlling the application of the $SpO_2$ waveforms to the modulator and the application of actuating current to said one or more diodes, and the application of the signals to the display.*

*60. An apparatus for testing a pulse oximeter having an optical sensor that senses $SpO_2$ values of living tissue, an electrical driver that produces an electrical signal that activates the optical sensor, and a signal processor responsive to the optical sensor that produces an oximeter signal corresponding to the $SpO_2$ value being sensed, said testing apparatus comprising:*

[[*for*]] first *testing circuitry that is responsive to the signal from the electrical driver in the oximeter, that generates first electrical test signals that are $SpO_2$ waveforms simulating those generated by the probe of the oximeter when the oximeter is used to check the blood oxygen level of a patient, and that transmits said first signals to the signal processor of the oximeter independently of the optical sensor,*

*second testing circuitry that generates second electrical test signals, that transmits the second electrical test signals to the optical sensor in the oximeter independently of the electrical driver of the oximeter, and that receives response signals from said optical sensor in response to transmission of the second test signals, and*

*a display that provides an indication of said response signals from the second testing circuitry.*

*61. The testing apparatus of claim 60,*

*wherein the first testing circuitry includes an electrical sensor that receives the electrical signal from the electrical driver and produces an output, a modulator that is connected to the electrical sensor and generates the selected first electrical test signals respectively representative of selected $SpO_2$ waveforms in response to the output from the electrical sensor, and a tester driver that is connected to the modulator and transmits said first signals to the signal processor in the oximeter.*

*62. The apparatus of claim 61,*

*wherein the first testing circuitry includes an electronic memory that stores an $SpO_2$ profile including a plurality of said $SpO_2$ waveforms; and*

*wherein the modulator modulates said electrical test signals with selected $SpO_2$ profiles and provides modulated electrical test signals representative of selected $SpO_2$ profiles.*

*63. The testing apparatus of claim 60,*

*wherein the second testing circuitry includes a source of current that generates the second electrical test signals, electrical connections that transmit the second electrical test signals to the optical sensor, an electrical sensors that receive the response signals from the optical sensor, and*

*wherein the display is connected to the electrical sensors of the second testing circuitry and produces said indication from the output of the electrical sensors.*

*64. The apparatus of claim 60,*

*wherein there is a housing enclosing both the first and second testing circuitry, and*

*wherein there are spaced first and second connectors in the housing respectively connected to the first and second testing circuitry and respectively adapted to be connected to the signal processor and the optical sensor.*

*65. The apparatus of claim 60,*

*wherein there is a microprocessor that controls the first and second testing circuitry in testing the signal processor and the optical sensor.*

*66. The apparatus of claim 60 for testing a pulse oximeter the optical sensor of which has an LED circuit, a photodiode circuit, and an oximeter connector providing LED and photodiode terminals respectively connected to the LED circuit and photodiode circuits,*

*wherein the second testing circuitry includes LED testing circuitry, photodiode testing circuitry, and a tester connector having LED and photodiode terminals respectively connected to the LED testing circuitry and photodiode testing circuitry, the LED and photodiode terminals in the tester connector corresponding to the LED and photodiode terminals of the oximeter connector, so that when the tester connector is connected to the oximeter connector, the LED testing circuitry and photodiode testing circuitry are respectively connected to the LED circuit and the photodiode circuits.*

*67. An apparatus for testing the probe of a pulse oximeter, said probe including an LED, a photodiode, and a probe connector with LED and photodiode terminals respectively connected to the LED and photodiode, the testing apparatus comprising:*

*a tester connector having LED and photodiode terminals capable of connecting to LED and photodiode terminals of the probe connector;*

*a signal source that generates probe testing signals and that is connected to predetermined terminals of the tester connector for applying testing signals on the said predetermined terminals so that the testing signals will be applied to the probe when the tester connector is connected to the probe connector;*

*a signal sensor that is connected to certain terminals of the tester connector, that is responsive to outputs thereon resulting from application of the probe testing signals to the probe, and that generates output signals representative of the outputs from the probe; and*

*a display connected to the signal sensor for displaying an indication of said output signals, thereby to test the operability of the probe.*

*68. The apparatus of claim 67, the probe having LED and photodiode circuits respectively including the LED and the photodiode,*

*wherein the signal source generates probe continuity testing signals at the LED and photodiode terminals of the tester connector;*

*wherein the signal sensor is connected to the LED and photodiode terminals of the tester connector, is responsive to continuity outputs on said LED and photodiode terminals resulting from the continuity testing signals, and generates continuity output signals representative of the continuity of the LED and photodiode circuits; and*

*wherein the display shows an indication of the continuity of the LED and photodiode circuits.*

*69. The apparatus of claim 67,*

*wherein the signal source generates probe sensitivity testing signals at the LED terminals of the tester connector;*

*wherein the signal sensor is connected to the photodiode terminals of the tester connector, is responsive to sensitivity outputs on said photodiode terminals resulting from the sensitivity testing signals, and generates sensitivity output signals representative of the sensitivity of the probe; and*

*wherein the display shows an indication of the sensitivity of the probe.*

*70. The apparatus of claim 69, the probe having red and IR LEDs,*

*wherein the probe sensitivity signals generated by the signal source are high and low current signals for the red LED and high and low current signals for the IR LED, thereby to enable high and low red outputs and high and low IR outputs to be generated by the photodiode when the tester connector is connected to the probe connector;*

*wherein the signal sensor is responsive to the high and low red outputs and generates red difference signals representing the difference between said high and low red outputs;*

*wherein the signal sensor is responsive to the high and low IR outputs and generates IR difference signals representing the difference between said high and low IR outputs; and*

*wherein the display is responsive to the red and IR difference signals and displays an indication thereof to indicate the sensitivity of the red and IR LEDs.*

*71. A method for testing the continuity of a pulse oximeter probe that includes an LED circuit and a photodiode circuit, said method involving the use of a tester having a tester connector providing terminals connected to an electrically actuating source and a sensor in the tester, and a probe connector providing terminals connected to said circuits, comprising the steps of:*

*connecting the tester connector to the probe connector and thereby simultaneously connecting the electrically activating source and the sensor to the LED and photodiode circuits,*

*electrically activating each of said circuits with said source,*

*sensing each circuit with said sensor for outputs in response to said electrical activation,*

*producing indications of outputs that are sensed, and*

*determining the continuity of the circuits from said indications.*

*72. A method for testing the sensitivity of a pulse oximeter probe that has red and IR LED circuits and a photodiode circuit including a photodiode, said method involving the use of a tester having a tester connector providing terminals connected to an electrically actuating source and a sensor in the tester, and a probe connector providing terminals connected to said circuits, comprising the steps of:*

*connecting the tester connector to the probe connector and thereby simultaneously connecting the electrically activating source and the sensor to the LED and photodiode circuits,*

*electrically activating the LED circuits with said sensors,*

*sensing the photodiode circuit with the sensor for outputs in response to said electrical activation,*

*producing indications of outputs that are sensed, and determining the sensitivity of the photodiode from said indications.*

*73. A pulse oximeter testing apparatus for testing a pulse oximeter having an optical sensor that senses $SpO_2$ values of living tissue, an electrical driver that produces an electrical signal that activates the optical sensor, and a signal processor responsive to the optical sensor that produces an oximeter signal corresponding to the $SpO_2$ value being sensed, said testing apparatus comprising:*

*a current sensor that is responsive to the electrical signal from the electrical driver in the oximeter and produces simulated red and IR signals;*

*an electronic memory storing $SpO_2$ waveforms that simulate $SpO_2$ waveforms in living tissue like those produced by the optical sensor in the normal operation of the oximeter;*

*a modulator responsive to the simulated red and IR signals from the current sensor, modulating the simulated red and IR signals with selected simulated $SpO_2$ waveforms from the memory, and generating modulated test signals respectively representative of the selected $SpO_2$ waveforms in living tissue; and*

*a tester driver responsive to the modulated test signals from the modulator, that produces electrical test signals representative of the selected $SpO_2$ waveforms, and that transmits the test signals to the signal generator in the oximeter to test the ability of the signal processor to process said representative $SpO_2$ waveforms and produce oximeter signals corresponding to the selected simulated $SpO_2$ waveforms.*

*74. The combination of a pulse oximeter and a testing apparatus, the oximeter having a signal processor, a display and a probe, the probe normally receiving signals from the oximeter and delivering modulated human signals to the signal processor resulting from a human finger or other body part placed in the probe,*

*wherein the testing apparatus is connected to the oximeter in place of the probe;*

*wherein the tester thereby receives the signals from the oximeter that would normally be delivered to the probe;*

*wherein the testing apparatus includes an electronic memory containing a database of waveforms corresponding to those produced by human fingers or other body parts when placed in the probe of an oximeter;*

*wherein the testing apparatus also includes a modulator that modulates the signals received by the testing apparatus with selected waveforms from the electronic memory thereby generating modulated testing signals that simulate the modulated human signals resulting from a human finger or other body part placed in the probe when the oximeter is in its normal use;*

*wherein the testing apparatus delivers the modulated testing signals to the signal processor;*

*wherein the* [[*modulating*]] modulated *testing signals are processed by the signal processor as if the modulated testing signals were the* [[*modulating*]] modulated *human signals thereby producing processed signals; and*

*wherein the processed signals are displayed on the display whereby comparisons can be made with known values.*

*75. An apparatus for testing a pulse oximeter having an optical sensor that senses $SpO_2$ values of living tissue, an LED driver, a signal processor responsive to the optical sensor that produces an oximeter signal corresponding to the $SpO_2$ value being sensed and a display, said testing apparatus comprising:*

*first means for testing the LED driver and the signal processor of the oximeter separately from the optical sensor of the oximeter, the display in the oximeter displaying the results of the first testing means;*

*second means for testing the optical sensor of the oximeter separately from the LED driver and the signal processor of the oximeter; and*

*means for displaying the results of the second testing means.*

*76. An apparatus for testing a pulse oximeter having an optical sensor that senses $SpO_2$ values of living tissue, a signal processor responsive to the optical sensor that produces an oximeter signal corresponding to the $SpO_2$ value being sensed, and a display that displays the said $SpO_2$ values sensed, the testing apparatus comprising:*

*means for testing the signal processor of the oximeter with testing $SpO_2$ values independently of the optical sensor; and*

*means for enabling a comparison of the testing $SpO_2$ values with the $SpO_2$ values displayed on the oximeter display.*

*77. An oximeter probe tester for an oximeter probe having LED and photodiode circuits, comprising:*

*means for electrically activating the LED circuit and the photodiode circuit of the oximeter probe so as to produce electrical test output signals in the circuits that are representative of the continuity of the circuits,*

*means for sensing whether or not the test output signals are present in the circuits, and*

*means for displaying an indication of the test output signals sensed.*

*78. An oximeter probe tester for an oximeter probe having a LED circuit including LEDs and a photodiode circuit including a photodiode, comprising:*

*means for electrically activating the LEDs of the oximeter probe so as to produce electrical test output signals in the photodiode that are representative of the sensitivity of the photodiode,*

*means for sensing the test output signals, and*

*means for displaying an indication of the test output signals sensed.*

*79. An oximeter probe tester for an oximeter probe having an LED circuit including LEDs and a photodiode circuit including a photodiode, comprising:*

*means for electrically activating the LED circuit and the photodiode circuit of the oximeter probe so as to produce electrical test output signals in the circuits that are representative of the continuity of the circuits,*

*means for sensing whether or not the test output signals are present in the circuits,*

*means for electrically activating the LEDs of the oximeter probe so as to produce electrical test output signals on the photodiode that are representative of the sensitivity of the photodiode,*

*means for sensing the test output signals on the photodiode, and*

*means for selectively and separately displaying an indication of the test output signals that are representative of the continuity of the circuits and the test output signals that are representative of the sensitivity of the photodiode.*

*80. The apparatus of claim 54,*

*wherein the red testing signals are red difference signals that represent the difference between the red high and red low outputs from the photodiode; and*

*wherein the IR testing signals are IR difference signals that represent the difference between the IR high and IR low outputs of the photodiode.*

*81. The apparatus of claim 80,*

*wherein the red and IR testing signals also include ratio signals that represent the ratio of the red difference signals to the IR difference signals.*

*82. A method for testing a pulse oximeter with a testing instrument wherein the oximeter includes a probe, an LED driver, a signal processor, an oximeter interface connector connected to the signal processor and the LED driver, the probe including LEDs, a photodiode, and a probe connector connected to the oximeter interface connector in normal use of the oximeter, the LEDs being responsive to LED drive signals from the LED driver and the photodiode generating $SpO_2$ waveforms for delivery to the signal processor through the oximeter interface connector when the probe is attached to the human being, and wherein the testing instrument includes a housing, a probe testing connector mounted on the housing, and a simulator testing connector mounted on the housing, the method comprising the steps of:*

*connecting either the probe connector alone to the probe testing connector, the simulator testing connector alone to the oximeter interface connector, or both the probe connector and the simulator testing connector, respectively, to the probe testing connector and the oximeter interface connector;*

*with the simulator testing connector to the oximeter interface connector in place of the probe, generating first test signals representative of $SpO_2$ waveforms that simulate said human $SpO_2$ waveforms generated by the probe in response to said LED drive signals;*

*transmitting the first test signals to the signal processor trough the interconnected simulator testing connector and oximeter interface connector;*

*with the probe connector connected to the probe testing connector instead of to the oximeter interface connector, generating a second test signal independently of the LED driver;*

*transmitting the second test signal to the probe through the interconnected probe connector and probe testing connector;*

*receiving an output from the probe in response to the second test signal; and*

*displaying said output.*

*83. A method for testing either the continuity or the sensitivity or both of a pulse oximeter probe that has an LED circuit including red and IR LEDs, a photodiode circuit including a photodiode, and a probe connector, the method involving the use of a housing enclosing electrically activating sources and signal sensing circuitry and mounting a probe testing connector providing LED and photodiode terminals connected to the electrically activating sources and the signal sensing circuitry, the method comprising the steps of:*

*interconnecting the probe connector and the probe testing connector and thereby interconnecting the LED and photodiode terminals and the LED and photodiode circuits respectively;*

*electrically activating both of the LED and photodiode circuits with an electrical activating source in the housing if continuity is being tested;*

*electrically activating only the LED circuits with an electrical activating source in the housing if sensitivity is being tested;*

*sensing both of the LED and photodiode circuits for outputs in response to said electrical activation if continuity is being tested;*

*sensing the photodiode circuit for outputs in response to said electrical activation if sensitivity is being tested;*

*displaying visual indications of the outputs that are sensed, and*

*determining the continuity and/or sensitivity of the probe from said visual indications.*

84. A method for isolating defects among certain parts of pulse oximeters by enabling said parts to be tested separately, each such oximeter having two principal parts, namely, a main instrument and a probe respectively connected to a main interface connector and a probe interface connector, the interface connectors being separately connected to each other in the normal operation of an oximeter when monitoring the SpO2 values of living tissue wherein the probe produces SpO2 waveforms of the living tissue being monitored and transmits those waveforms to the main instrument to indicate thereon certain characteristics of said waveforms, the method involving the use of a testing apparatus that includes a simulator that can be drive to generate simulated SpO2 waveforms corresponding to those produced by the probe in said normal operation and a signal processor driver capable of driving the main instrument of the oximeter like the probe does in said normal operation, the testing apparatus further including a probe driver-sensor unit capable of activating the probe and sensing responses therefrom, a housing enclosing the simulator, the signal processor driver, and the probe driver-sensor unit, first and second testing interface connectors mounted on the housing, a display mounted on the housing and connected to the probe driver-sensor unit to display indications of characteristics of said responses, and a microprocessor in the housing connected to the simulator, the probe driver-sensor unit, and the display for controlling the actions thereof, the method comprising the steps of:

connecting either the main interface connector to the first testing interface connector, or the probe interface connector to the second testing interface connector, or both the main interface connector and the probe interface connector respectively to the first and second testing interface connectors, if the main interface connector is connected to the first testing interface connector, causing the main instrument to drive the simulator and cause the signal processor driver to drive the main instrument which in turn causes an indication of the characteristics of the simulated waveforms on the main instrument, if the probe interface connector is connected to the second testing interface connector, causing the probe driver-sensor to activate the probe and cause responses therefrom to be sensed and indications thereof to be displayed on said display, and if both the main and probe interface connectors are both connected to the first and second testing interface connectors, causing the main instrument to drive the simulator and cause the signal processor drive to drive the main instrument which in turn causes an indication of the characteristics of the simulated waveforms on the main instrument, and causing the probe driver-sensor to activate the probe and cause responses therefrom to be sensed and indications thereof to be displayed on the display.

85. A method for isolating defects among certain parts of pulse oximeters by enabling said parts to be tested separately, each such oximeter having two principal parts, namely, a main instrument and a probe, each such main instrument including as subsidiary parts a signal processor and an LED driver connected to an main interface connector, and each such probe including as subsidiary parts an LED circuit including red and IR LEDs and a photodiode circuit including a photodiode, said circuits terminating in a probe interface connector, the interface connectors of a main instrument and a probe being separately interconnected in the normal operation of an oximeter when monitoring the SpO2 values of living tissue wherein the LED driver activates the LEDs which in turn activate the photodiode and cause the photodiode to produce SpO2 waveforms of the living tissue being monitored and to transmit those waveforms to the signal processor that in turn drives the display to indicate certain characteristics of said waveforms, the method involving the use of a testing apparatus that includes a simulator that can be driven to generate simulated SpO2 waveforms corresponding to those produced by the photodiode in said normal operation and a signal processor driver capable of driving the signal processor of the oximeter like the photodiode does in said normal operation, the testing apparatus further including a probe driver-sensor unit capable of activating the LED and photodiode circuits and sensing responses therefrom, a housing enclosing the simulator, the signal processor driver, and the probe driver-sensor unit, first and second testing interface connectors mounted on the housing, the first testing interface connector being connected to the simulator and the signal processor driver and the second testing interface connector being connected to the probe driver-sensor unit, a display mounted on the housing and connected to the probe driver-sensor unit to display indications of the characteristics of said responses, and a microprocessor in the housing connected to the simulator, the probe driver-sensor unit, and the display for controlling the actions thereof, the method comprising the steps of:

connecting either the main interface connector to the first testing interface connector, or the probe interface connector to the second testing interface connector, or both the main interface connector and the probe interface connector respectively to the first and second testing interface connectors, if the main interface connector is connected to the first testing interface connector, causing the LED driver to drive the simulator and cause the signal processor driver to drive the signal processor which in turn drives the display of the oximeter with an indication of the characteristics of the simulated waveforms, if the probe interface connector is connected to the second testing interface connector, causing the probe driver-sensor to activate the LED and photodiode circuits and cause responses therefrom to be sensed and indications thereof to be displayed on the display of the testing apparatus, and if both the main and probe interface connectors are both connected to the first and second testing interface connectors, causing the LED driver to drive the simulator and cause the signal processor driver to drive the signal processor which in turn drives the display of the oximeter with an indication of the characteristics of the simulated waveforms and causing the probe driver-sensor to active the LED and photodiode circuits and cause responses therefrom to be sensed and indications thereof to be displayed on the display of the testing apparatus.

86. The method of claim 85, wherein if the probe interface connector is connected to the second testing interface connector, causing the probe driver-sensor to activate the LED and photodiode circuits with continuity signals thereby causing the responses to be indicative of the continuity of said circuits.

87. The method of claim 85, wherein if the probe interface connector is connected to the second testing interface connector, causing the probe driver-sensor to activate the LED circuit with sensitivity signals which in turn activates the photodiode circuit thereby causing the responses to be indicative of the sensitivity of said circuits.

88. The method of claim 83, wherein the electrical activation of only the LED circuits involves applying high and low signals to the LED circuits thereby producing high and low outputs in the photodiode circuit;

generating difference signals from said high and low signals; and determining the sensitivity of the probe from said difference signals.

89. A method for testing the sensitivity of a pulse oximeter probe which provides red and infrared LEDs and a photodiode, comprising the steps of:

measuring the output of the photodiode as it relates to one LED at different input levels to said one LED and producing a difference signal therefrom;

measuring the output of the photodiode as it relates to the other LED at different input levels to said other LED and producing a difference signal therefrom; and displaying indications of said difference signals.

90. The method of claim 89, wherein each measuring step involves causing each of the LEDs to be driven with different inputs and measuring the output from the photodiode resulting therefrom.

91. A method for testing the sensitivity of a pulse oximeter probe which provides red and infrared LEDs and a photodiode, comprising the steps of:

obtaining high and low outputs from the photodiode that relate to one of the LEDs;

measuring the high and low outputs from the photodiode relating to said one LED and producing a difference signal;

obtaining high and low outputs from the photodiode that relate to the other LED;

measuring the high and low outputs from the photodiode relating to said other LED and producing a difference signal; and determining the sensitivity of the probe from said difference signals.

92. The method of claim 91, wherein obtaining the outputs of the photodiode that relate to said one LED is in response to causing said one LED to be activated at high and low levels; and wherein obtaining the outputs of the photodiode that relate to said other LED is in response to causing said other LED to be activated at high and low levels.

* * * * *